US007622441B2

(12) United States Patent
Mickle et al.

(10) Patent No.: US 7,622,441 B2
(45) Date of Patent: Nov. 24, 2009

(54) SUSTAINED RELEASE PHARMACEUTICAL COMPOUNDS TO PREVENT ABUSE OF CONTROLLED SUBSTANCES

(75) Inventors: Travis Mickle, Charlottesville, VA (US); Suma Krishnan, Blacksburg, VA (US); James Scott Moncrief, Christiansburg, VA (US); Christopher Lauderback, Blacksburg, VA (US); Thomas Piccariello, Blacksburg, VA (US)

(73) Assignee: Shire LLC, Florence, KY (US)

( * ) Notice: Subject to any disclaimer, the term of this patent is extended or adjusted under 35 U.S.C. 154(b) by 716 days.

(21) Appl. No.: 10/923,257

(22) Filed: Aug. 23, 2004

(65) Prior Publication Data

US 2005/0080012 A1 Apr. 14, 2005

Related U.S. Application Data

(63) Continuation-in-part of application No. PCT/US03/05525, filed on Feb. 24, 2003.

(60) Provisional application No. 60/362,082, filed on Mar. 7, 2002, provisional application No. 60/358,368, filed on Feb. 22, 2002.

(51) Int. Cl.
*A61K 38/00* (2006.01)
*A61K 51/00* (2006.01)
*A61K 38/04* (2006.01)
*A61K 38/06* (2006.01)

(52) U.S. Cl. ........................ 514/12; 424/1.69; 530/330; 530/331

(58) Field of Classification Search .................... 514/12
See application file for complete search history.

(56) References Cited

U.S. PATENT DOCUMENTS 3,843,696 A 10/1974 Wagner et al.
3,846,399 A 11/1974 Hirschmann et al.
3,878,187 A 4/1975 Schneider et al.
3,884,898 A 5/1975 Schneider
3,975,342 A 8/1976 Gross
3,998,799 A 12/1976 Bodor et al.
4,025,501 A 5/1977 Leute
4,040,907 A 8/1977 Ullman et al.
4,297,346 A 10/1981 Rips et al.
4,356,166 A 10/1982 Peterson et al.
4,399,121 A 8/1983 Albarella et al.
4,427,660 A 1/1984 Schiffman et al.
4,457,907 A 7/1984 Porter
4,552,864 A 11/1985 Antoni et al.
4,650,675 A 3/1987 Borel et al.
4,801,575 A 1/1989 Pardridge
4,863,735 A 9/1989 Kohn et al.
4,902,505 A 2/1990 Pardridge et al.
4,960,790 A 10/1990 Stella et al.
4,976,962 A 12/1990 Bichon et al.
5,026,827 A 6/1991 Miyazaki et al.
5,073,641 A 12/1991 Bundgaard et al.
5,087,616 A 2/1992 Myers et al.
5,169,933 A 12/1992 Anderson et al.
5,183,883 A 2/1993 Tanaka et al.
5,219,564 A 6/1993 Zalipsky et al.
5,238,714 A 8/1993 Wallace et al.
5,362,831 A 11/1994 Mongelli et al.
5,501,987 A 3/1996 Ordonez et al.
5,529,915 A 6/1996 Phillips et al.
5,534,496 A 7/1996 Lee et al.
5,670,477 A 9/1997 Poduslo et al.
5,762,909 A 6/1998 Uzgiris
5,767,227 A 6/1998 Latham et al.
5,846,743 A 12/1998 Janmey et al.
5,851,536 A 12/1998 Yager et al.
5,882,645 A 3/1999 Toth et al.
5,891,459 A 4/1999 Cooke et al.
5,898,033 A 4/1999 Swadesh et al.
5,910,569 A 6/1999 Latham et al.
5,948,750 A 9/1999 Garsky et al.
5,952,294 A 9/1999 Lazo et al.
5,977,163 A 11/1999 Li et al.
6,005,004 A 12/1999 Katz et al.

(Continued)

FOREIGN PATENT DOCUMENTS

AU 54168/65 1/1965

(Continued)

OTHER PUBLICATIONS

Hughes, et al. Lipidic Peptides. II1: Lipidic Amino Acid and Oligomer Conjugates of Morphine, Journal of Pharmaceutical Sciences, vol. 80, No. 12, Dec. 1991 (cited in IDS of Oct. 23, 2007).*

(Continued)

*Primary Examiner*—Maury Audet
(74) *Attorney, Agent, or Firm*—Darby & Darby

(57) ABSTRACT

The present invention provides methods for altering controlled substances in a manner that decreases their potential for abuse. The novel compounds may be combined in tablets with suitable excipients or formulated in solution for oral delivery. When delivered by the oral route the controlled substance is released in a time-dependent manner (sustained release) by acid hydrolysis and/or enzymatic cleavage. When administered by injection the controlled substance is released in a time-dependent manner (sustained release) by way of serum enzymes.

2 Claims, 22 Drawing Sheets

U.S. PATENT DOCUMENTS

| | | | |
|---|---|---|---|
| 6,030,941 | A | 2/2000 | Summerton et al. |
| 6,043,230 | A | 3/2000 | Arimilli et al. |
| 6,048,736 | A | 4/2000 | Kosak |
| 6,074,659 | A | 6/2000 | Kunz et al. |
| 6,093,391 | A | 7/2000 | Kabanov et al. |
| 6,235,718 | B1 | 5/2001 | Balasubramanium et al. |
| 6,255,285 | B1 | 7/2001 | Kotake |
| 6,306,993 | B1 | 10/2001 | Rothbard et al. |
| 6,309,633 | B1 | 10/2001 | Ekwuribe et al. |
| 6,458,842 | B1 | 10/2002 | Dickinson et al. |
| 6,740,641 | B2 | 5/2004 | Gao |
| 6,784,186 | B1 | 8/2004 | Jackson |
| 2001/0031873 | A1 | 10/2001 | Greenwald et al. |
| 2002/0098999 | A1 | 7/2002 | Gallop et al. |
| 2002/0099013 | A1 | 7/2002 | Piccariello et al. |
| 2002/0151526 | A1 | 10/2002 | Gallop et al. |
| 2002/0151529 | A1 | 10/2002 | Cundy et al. |
| 2002/0164373 | A1 * | 11/2002 | Maloney ..................... 424/469 |
| 2003/0077297 | A1 | 4/2003 | Chen et al. |
| 2003/0091593 | A1 | 5/2003 | Bachmann et al. |
| 2004/0204434 | A1 | 10/2004 | Shafer |

FOREIGN PATENT DOCUMENTS

| | | |
|---|---|---|
| EP | 0 187 547 A2 | 7/1987 |
| FR | 1421130 | 1/1965 |
| GB | 1092089 | 11/1967 |
| GB | 1112347 | 5/1968 |
| WO | WO 94/11021 A | 5/1994 |
| WO | WO 95/12605 | 5/1995 |
| WO | WO 95/14033 | 5/1995 |
| WO | WO 97/36616 | 10/1997 |
| WO | WO 98/04277 | 2/1998 |
| WO | WO 00/37103 A | 6/2000 |
| WO | WO 02/34237 A1 | 5/2002 |

OTHER PUBLICATIONS

Supplementary European Search Report for EP 01273387 dated Sep. 28, 2004.

Thomson Derwent World Patents Index.

International Search Report for PCT/US03/05524 dated Feb. 24, 2003.

International Search Report for PCT/US03/05525 dated Oct. 9, 2003.

International Search Report for PCT/US04/17204 dated Oct. 15, 2004.

Aggarwal, et al., "Synthesis and Biological Evaluation of Prodrugs of Zidovudine," *J. Med. Chem.*, 33(5):1505-1511 (1990).

Amidon, G., et al., "A Theoretical Basis for a Biopharmaceutic Drug Classification: The Correlation of in Vitro Drug Product Dissolution and in Vivo Bioavailability," *Pharmaceutical Research*, vol. 12, No. 3 (1995).

Amidon, G.L., et al., "5'-Amino Acid Esters of Antiviral Nucleosides, Acyclovir, and AZT are Absorbed by the Intestinal PEPT1 Peptide Transporter," *Pharm Res*, 16(2):175 (1999), Abstract.

Balimane, P., et al., "Effect of Ionization on the Variable Uptake of Valacyclovir via the Human Intestinal Peptide Transporter (hPepT1) in CHP cells," *Biopharm Drug Dispos*, 21(5):165-174 (2000), Abstract.

Balimane, P.V., et al., "Direct Evidence for Peptide Transporter (PepT1)-Mediated Uptake of a Nonpeptide Prodrug, Valacyclovir," *Biochem Biophys Res Commun*, 250(2):246-251 (1998), Abstract.

Bunevicius, R., "Effects of Thyroxine as Compared with Thyroxine Plus Triiodothyronine in Patients with Hypothyroidism," *The New England Journal of Medicine*, vol. 340, No. 6 (1999).

Burnette, Thimysta C., et al., "Metabolic Disposition of the Acyclovir Prodrug Valaciclovir in the Rat," *Drug Metabolism and Disposition*, 22(1):60-64 (1994).

Canaris, G., "The Colorado Thyroid Disease Prevalence Study," Archives Internal Medicine Articles and Abstracts, vol. 160, No. 4 (2000).

De Vrueh, Remco L.A., et al, "Transport of L-Valine-Acyclovir Via the Oligopeptide Transporter in the Human Intestinal Cell Line, Caco-2," *Journal of Pharmacology and Experimental Therapeutics*, 286(2):1166-1170 (1988).

Friedrichsen, G.M., et al., "Model Prodrugs Designed for the Intestinal Peptide Transporter. A Synthetic Approach for Coupling of Hydroxy-Containing Compounds to Dipeptides," *Eur J Pharm Sci*, 14(1):13-19 (2001, Abstract.

Guo, A., et al., "Interactions of a Nonpeptidic Drug, Valacyclovir, with the Human Intestinal Peptide Transporter (hPEPT1) Expressed in a Mammalian Cell Line," *Pharmacol Exp Ther*, 289(1):448-454 (1999), Abstract.

Han H., et al., "5'-Amino Acid Esters of Antiviral Nucleosides, Acyclovir, and AZT and Absorbed by the Intestinal PEPT1 Peptide Transporter," *Pharm Res*, 15(8):1154-1159 (1998), Abstract.

Han, H.K., et al., "Cellular Uptake Mechanism of Amino Acid Ester prodrugs in Caco-2hPEPT1 Cells Overexpressing a Human Peptide Transporter," *Pharm Res*, 15(9):1382-1386 (1998), Abstract.

Han, Hyo-Kyung, et al., "Targeted Prodrug Design to Optimize Drug Delivery," *AAPS PharmSci*, 2(1): Article 6 (2000).

Havranova, Marie et al., "A High-Molecular Mass Derivative of Trypsin-Kallikrein Inhibitor for Potential Medical Use, II," *Hoppe-Seyler's Z. Physiol. Chem.*, 363:295-303 (1982).

Herrera-Ruiz, D., et al., "Spatial Expression Patterns of Peptide Transporters in the Human and Rat Gastrointestinal Tracts, Caco-2 in vitro Cell Culture Model, and Multiple Human Tissues," *AAPS PharmSci*, 3(1):E9 (2001), Abstract.

Hosztafi, S. et al. "Synthesis and Analgetic Activity of Nicotinic Esters of Morphine Derivatives," Arzneim.-Forsch./Drug Res. 43(II), Nr. 11 (1993).

International Search Report, dated Oct. 9, 2003, for PCT/US03/05525.

International Search Report, dated Sep. 3, 2003.

Knutter, I, et al., "A Novel Inhibitor of the Mammalian Peptide Transporter PEPT1," *Biochemistry*, 40(14):4454-4458 (2001), Abstract.

Kovacs, J., et al., "Glutamic and Aspartic Anhydrides. Rearrangement of N-Carboxyglutamic 1,5-Anhydride to the Leuchs' Anhydride and Conversion of the Latter to Pyroglutamic Acid."

Kramer, Werner et al., "Intestinal Absorption of Peptides by Coupling to Bile Acids," *The Journal of Biochemistry*, 269(14):10621-10627 (1994).

Leibach, F.H. et al., "Peptide Transporters in the Intestine and the Kidney," *Annu Rev Nutri*, 16:99-119 (1996), Abstract.

Li, Chun, et al., "Complete Regression of Well-Established Tumors Using a Novel Water-Soluble Poly(L-Glutamic Acid)-Paclitaxel Conjugate," *Cancer Res*, 58:2404-2409 (1998).

Marrio, Claudine, et al., "Amino Acid Sequence of the Unique 3,5,3'-Triiodothyronine-Containing Sequence from Porcine Thyroglobulin," *Biochemical and Biophysical Research Communications*, 112(1):206-213 (1983).

Negishi, Naoki , et al., "Coupling of Naltrexone to Biodegradable Poly ($\alpha$-Amino Acids)," *Pharmaceutical Research*, 4(4):305-310 (1987).

Nishida, Koyo, et al., "Pharmacokinetic Analysis of in Vivo Metabolism of Amino Acid or Dipeptide Conjugates of Salicylic Acid in Rabbit Intestinal Microorganisms," *Pharmaceutical Research*, 11(1):160-164 (1994).

Oh, D., et al., "Estimating the Fraction Dose Absorbed from Suspensions of Poorly Soluble Compounds in Humans: A Mathematical Model," *Pharmaceutical Research*, vol. 10, No. 2 (1993).

Oh, DM, et al., "Drug Transport and Targeting. Intestinal Transport," *Pharma Biotechnol*, 12:59-88 (1999), Abstract.

Okada, Masahiko, et al., "Synthesis of Glycopeptide-conjugates via Ring-Opening Polymerization of Sugar-Substituted $\alpha$-Amino Acid *N*-Carboxyanhydrides (GlycoNCAs)," *Proc. Japan Acad.*, 73:205-209 (1997).

Orten, James M. et al., "Thyroxine," *Human Biochemistry*, $9^{th}$ Ed., C.V. Mosby Company, St. Louis,pp. 401-405 (1975).

Pade, V., et al., "Link Between Drug Absorption Solubility and Permeability Measurements in Caco-2 Cells," *Journal of Pharmaceutical Sciences*, vol. 87, No. 12 (1998).

Rawitch, Allen B., et al., "The Isolation of Identical Thyroxine Containing Amino Acid Sequences from Bovine, Ovine and Porcine Thyroglobulins," *Biochemical and Biophysical Research Communications*, 118(2):423-429 (1984).

Ryser, Hugues J.P., et al., "Conjugation of Methotrexate to Poly (L-lysine) Increases Drug Transport and Overcomes Drug Resistance in Cultured Cells," *Proc. Natl. Acad. Sci. USA*, 75(8):3867-3870 (1978).

Sawada, Kyoko, et al., "Recognition of L-Amino Acid Ester Compounds by Rat Peptide Transporters PEPT1 and PEPT2," *Journal of Pharmacology and Experimental Therapeutics*, 291(2):705-709 (1999).

Schmidt, Brigitte F., et al., "Peptide-Linked 1,3-Dialkyl-3-acyltriazenes: Gastrin Receptor Directed Antineoplastic Alkylating Agents," *Journal of Medicinal Chemistry*, 37(22):3812-3817 (1994).

Shen, H., et al., "Developmental Expression of PEPT1 and PEPT2 in Rat Small Intestine, Colon, and Kidney," *Pediatr Res*, 49(6):789-795 (2001), Abstract.

Shiraga, T., et al., "Cellular and Molecular Mechanisms of Dietary Regulation on Rat Intestinal H+/Peptide Transporter PepT1," *Gastroenterology*, 116(2):354-362 (1999), Abstract.

Tamai, I., et al., "Improvement of L-dopa Absorption by Dipeptidyl Derivation, Utilizing Peptide Transporter PepT1," *J. Pharma. Sci.*, 87(12):1542-1546 (1988), Abstract.

Toft, A., "Thyroid Hormone Replacement—One Hormone or Two?," *The New England Journal of Medicine*, vol. 340, No. 6 (1999).

Toth, Istvan, "A Novel Chemical Approach to Drug Delivery: Lipidic Amino Acid Conjugates," *Journal of Drug Targeting*, 2:217-239 (1994).

Zunino, Franco, et al., "Anti-Tumor Activity of Daunorubicin Linked to Poly-L-Aspartic Acid," *International Journal of Cancer*, 30:465-470 (1982).

Zunino, Franco, et al., "Comparison of Antitumor Effects of Daunorubicin Covalently Linked to Poly-L-Amino Acid Carriers," *European Journal of Cancer & Clinical Oncology*, 20(3):121-125 (1984).

Hughes, et al. Lipidic Peptides. III: Lipidic Amino Acid and Oligomer Conjugates of Morphine, Journal of Pharmaceutical Sciences, vol. 80, No. 12, Dec. 1991.

* cited by examiner

Polyserine-Naltrexone
Naltrexone
ng/ml
Hours
0
5
10
15
20
25
30
35
40
45
50
0
5
10
15

Pro-Hydrocodone —Boc-Ala-OSu→ Boc-Ala-Pro-Hydrocodone —4N HCl in dioxane→ Ala-Pro-Hydrocodone

Figure 17

SEQUENCE LISTING

```
<160> NUMBER OF SEQ ID NOS: 9

<210> SEQ ID NO 1
<211> LENGTH: 5
<212> TYPE: PRT
<213> ORGANISM: artificial sequence
<220> FEATURE:
<223> OTHER INFORMATION: synthetic carrier

<400> SEQUENCE: 1

Gly Gly Gly Gly Leu
1               5
```

<210> SEQ ID NO 2
<211> LENGTH: 5
<212> TYPE: PRT
<213> ORGANISM: artificial sequence
<220> FEATURE:
<223> OTHER INFORMATION: synthetic carrier

<400> SEQUENCE: 2

Glu Glu Glu Glu Glu
1               5

<210> SEQ ID NO 3
<211> LENGTH: 5
<212> TYPE: PRT
<213> ORGANISM: artificial sequence
<220> FEATURE:
<223> OTHER INFORMATION: synthetic carrier

<400> SEQUENCE: 3

Gly Gly Gly Gly Ile
1               5

<210> SEQ ID NO 4
<211> LENGTH: 5
<212> TYPE: PRT
<213> ORGANISM: artificial sequence
<220> FEATURE:
<223> OTHER INFORMATION: synthetic carrier
<220> FEATURE:
<221> NAME/KEY: misc_feature
<223> OTHER INFORMATION: Aminoisobutyric Acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 4

Gly Gly Gly Gly Xaa
1               5

<210> SEQ ID NO 5
<211> LENGTH: 5
<212> TYPE: PRT
<213> ORGANISM: artificial sequence
<220> FEATURE:
<223> OTHER INFORMATION: synthetic carrier

<400> SEQUENCE: 5

Gly Gly Gly Gly Phe
1               5

<210> SEQ ID NO 6
<211> LENGTH: 5
<212> TYPE: PRT
<213> ORGANISM: artificial sequence
<220> FEATURE:
<223> OTHER INFORMATION: synthetic carrier

<400> SEQUENCE: 6

Gly Gly Glu Glu Glu
1               5

<210> SEQ ID NO 7
<211> LENGTH: 5
<212> TYPE: PRT
<213> ORGANISM: artificial sequence
<220> FEATURE:

-continued

```
<223> OTHER INFORMATION: synthetic carrier
<220> FEATURE:
<221> NAME/KEY: misc_feature
<223> OTHER INFORMATION: Aminoisobutyric Acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 7

Glu Glu Gly Gly Xaa
1               5


<210> SEQ ID NO 8
<211> LENGTH: 5
<212> TYPE: PRT
<213> ORGANISM: artificial sequence
<220> FEATURE:
<223> OTHER INFORMATION: synthetic carrier

<400> SEQUENCE: 8

Glu Glu Gly Gly Leu
1               5


<210> SEQ ID NO 9
<211> LENGTH: 5
<212> TYPE: PRT
<213> ORGANISM: artificial sequence
<220> FEATURE:
<223> OTHER INFORMATION: synthetic carrier

<400> SEQUENCE: 9

Glu Glu Gly Gly Ile
1               5
```

SUSTAINED RELEASE PHARMACEUTICAL COMPOUNDS TO PREVENT ABUSE OF CONTROLLED SUBSTANCES

CROSS REFERENCE RELATED APPLICATIONS

This application claims benefit under 35 U.S.C. 120 and is a continuation-in-part application of PCT application No. US03/05525 filed Feb. 24, 2003, which claims priority under 35 U.S.C. 119(e) to U.S. Provisional application No. 60/358,368 filed Feb. 22, 2002 and U.S. Provisional application No. 60/362,082 filed Mar. 7, 2002, all of which are hereby incorporated by reference in their entirety.

BACKGROUND OF THE INVENTION (i) Field of the Invention

The present invention relates to novel pharmaceutical compounds and more particularly to controlled substances that are covalently bound to a chemical moiety and thus rendered pharmaceutically inactive until broken down by enzymatic and/or chemical means in a time-dependent manner following oral administration. Delayed release from the conjugate prevents spiking of drug levels and affords gradual release over an extended period of time. The enzymatic and/or chemical conditions necessary for the release of the controlled substance are either not present or of minimal activity when the novel pharmaceutical compound is introduced nasally, inhaled, or injected; thus, also preventing spiking when administered by these routes. Controlled substances with these novel properties are less likely to be abused due to the diminished "rush" effect of the modified controlled substance. Consequently, the therapeutic value of these pharmaceuticals is enhanced by decreasing euphoria while increasing the duration of the analgesic effect.

(ii) Description of the Related Art

A number of pharmacologically useful compounds are also commonly abused controlled substances. In particular, analgesics that are prescribed for the management of acute and chronic pain have become increasingly abused over the last decades. For example, the increase in prescription of oxycodone in the last few years led to widespread abuse of this drug. Amphetamines are another example of controlled substances with important pharmacological uses that are highly addictive and commonly abused.

There is considerable information readily available to individuals which teaches how to derive purified forms of controlled substances from prescription products. These techniques are both simple and well described on multiple websites. Most of these procedures utilize cold water, although, hot water, changes in pH and other solvents are described. Examples of these procedures are described below.

The description of these procedures was found on the web in February of 2003 at http://codeine.50g.com/info/extraction.html#ex.coldw and is paraphrased below. Cold water extraction is used to extract an opiate/opioid substance from combination tablets. This method subverts the fact that opiates are generally very soluble in cold water, while paracetamol, aspirin, and ibuprofen are only very slightly soluble. These techniques are sophisticated enough to recognize that pseudoephedrine and caffeine are water soluble and will remain in the solution and that dispersible tablets make it difficult to extract secondary substances. The description of the equipment required makes it clear that these procedures make abuse readily available. The equipment includes a minimum two glasses or cups, paper filters (unbleached coffee filters will do) and a measure glass. Portions of the procedures are provided below:

1. Crush the tablets and dissolve in cold (20° C.) water.
2. Cool the solution down to approximately 5° C. stirring occasionally.
3. Leave the solution in a cool place for about 20 minutes.
4. Wet the filter(s) with very cold water to prevent it from absorbing the solution and put it in the glass. Stick an elastic/rubber band around the container to keep the filter in place.
5. Pour the solution through the filter to filter out the secondary substance from codeine.
6. Discard used filters with secondary substance solids left.

However, when these procedures were viewed as not providing sufficient yields improved method were designed for extracting codeine which simply require the addition of chloroform or like solvent such as methylene chloride. This technique utilizes methods which alter the pH aspects of the solution to improve extraction and even provides instruction on how to re-salt the product. Portions of the procedure are described below.

1. Place uncrushed T3's or other APAP/codeine product in a small glass or beaker and cover with enough distilled water so that the pills will break down into a thin paste.
2. Add dry sodium carbonate to reduce the codeine phosphate to codeine base. The pH of the mixture should be about 11 or greater.
3. Pour the mixture into the pyrex pan and rinse the beaker with a few ml of distilled water and add the rinse water to the mix in a pan.
4. Wrap the dried material in a coffee filter and grind the stuff
5. Pour the dry crushed mixture into a glass bottle with a screw-on top and pour in enough chloroform to completely cover.
6. Shake and filter.

While there has been considerable effort to provide controlled substances which are resistance to abuse current products fail to achieve the stability required to prevent abuse. The present invention however, provides methods and compositions which retain their stability even when subjected to current abuse methods, and therefore provide a much needed but less addictive and/or less likely to be abused product.

SUMMARY OF THE INVENTION

Thus, there is clearly a need in the art for a more "street-safe" version of controlled substances, which will permit one to obtain the therapeutically beneficial effects of these substances on the one hand while avoiding the euphoric effects that lead to substance abuse on the other hand. It is, therefore, a primary object of the present invention to fulfill this need by providing controlled substances that have been chemically modified to be released only under selected conditions and, even then, only at a controlled rate that does not give rise to a euphoric effect.

More particularly, it is an object of the present invention to provide chemically modified controlled release substances that are themselves inactive and resistant to absorption until broken down by chemical or enzymatic means at the desired target location, such as for example under the acidic conditions of the stomach and/or the enzymatic activity present in the gastrointestinal tract.

It is another object of the invention to provide chemically modified controlled release substances that are released only in the blood serum, again at controlled release rates that do not give rise to a euphoric effect.

In a first aspect, the present invention comprises a controlled substance that has been rendered inactive or substantially inactive comprising said controlled substance covalently bonded to a chemical moiety comprising an amino acid or more preferably an oligopeptide. The oligopeptide preferably less than 50 and more preferably less than 6 amino acids.

In a second aspect, the present invention comprises a controlled substance that has been rendered inactive or substantially inactive comprising said controlled substance covalently bonded to a chemical moiety comprising an amino acid or more preferably an oligopeptide which breaks down under the acid conditions of the stomach and/or the enzymatic activity present in the gastrointestinal tract.

In the oral composition define above, absorption of the controlled substance into the bloodstream upon oral delivery occurs in a sustained release manner and peak concentrations of the drug are decreased as compared to non-conjugated drug given in a similar dosage and formulation. Sustained release may further be defined as release of the active agent into systemic blood circulation over a prolonged period of time relative to the release of the active agent in conventional formulations through similar delivery routes.

In a third aspect, the present invention relates to a method for delivering a controlled substance to a patient so as to obtain a therapeutic, but not a substantial euphoric effect, comprising orally administering the above composition to the patient.

In a fourth aspect, the present invention relates to a method for delivering a controlled substance to a patient so as to obtain a therapeutic, but not a substantial euphoric effect, comprising parenterally administering the above composition to the patient.

The invention is further illustrated by drawings (figures) and tables of data. The following is a list of illustrations describing the invention in detail.

FIG. **8*a*** illustrates the synthetic protocol for amino acid conjugate of (s)-amphetamine.

FIG. **8*b*** illustrates the synthesis of deprotected conjugate.

Figure 9:
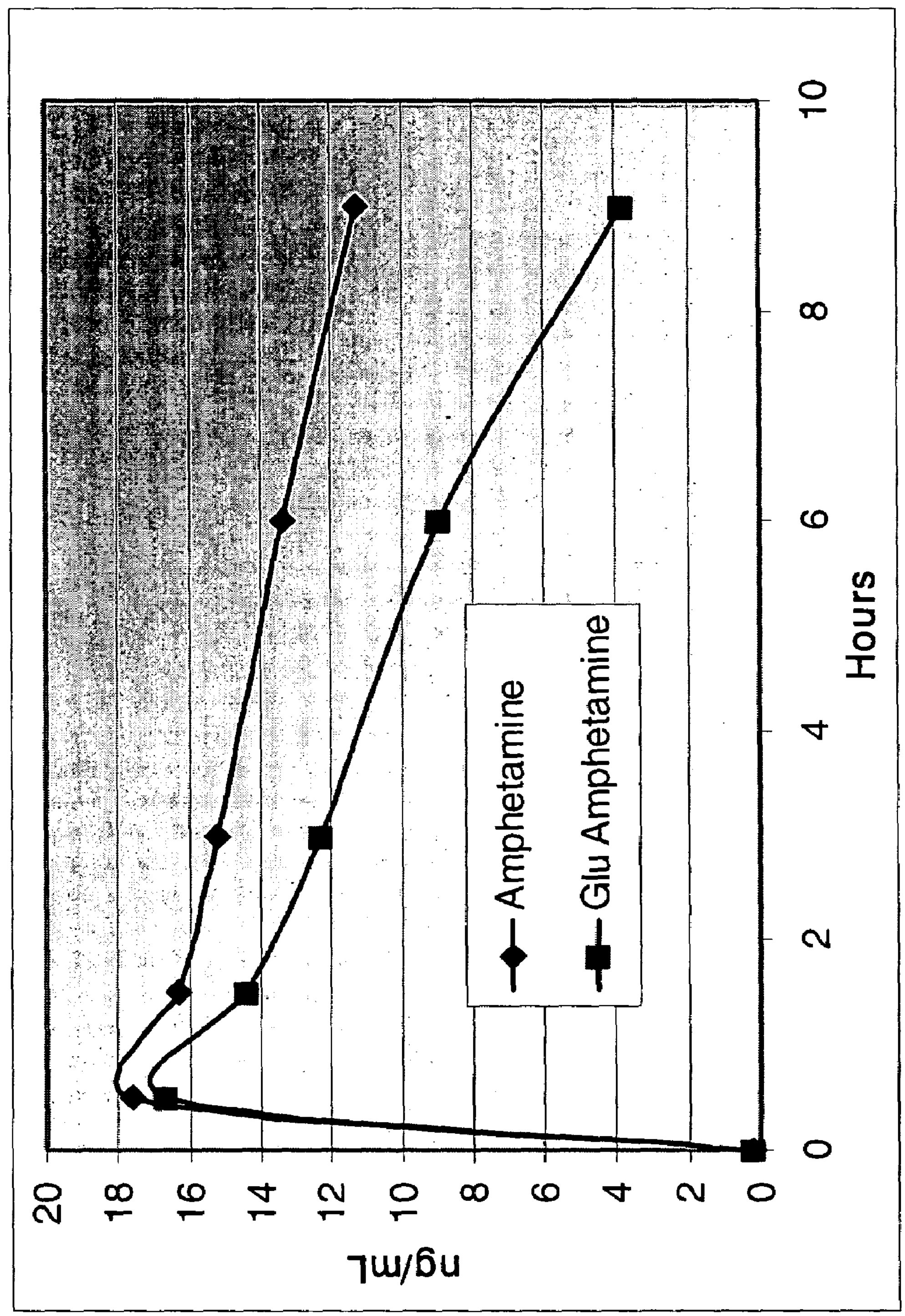
Figure 10:
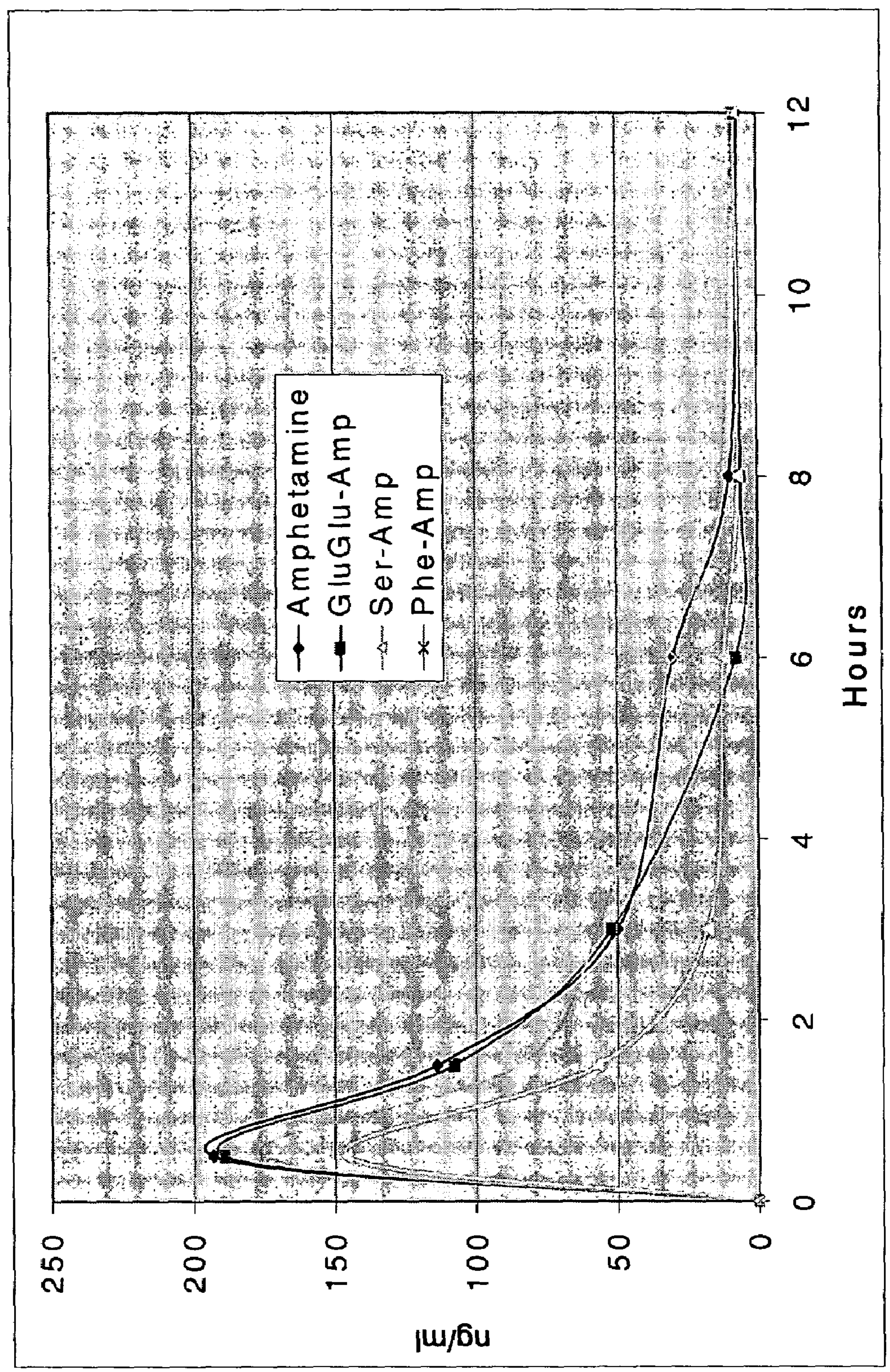
Figure 11:
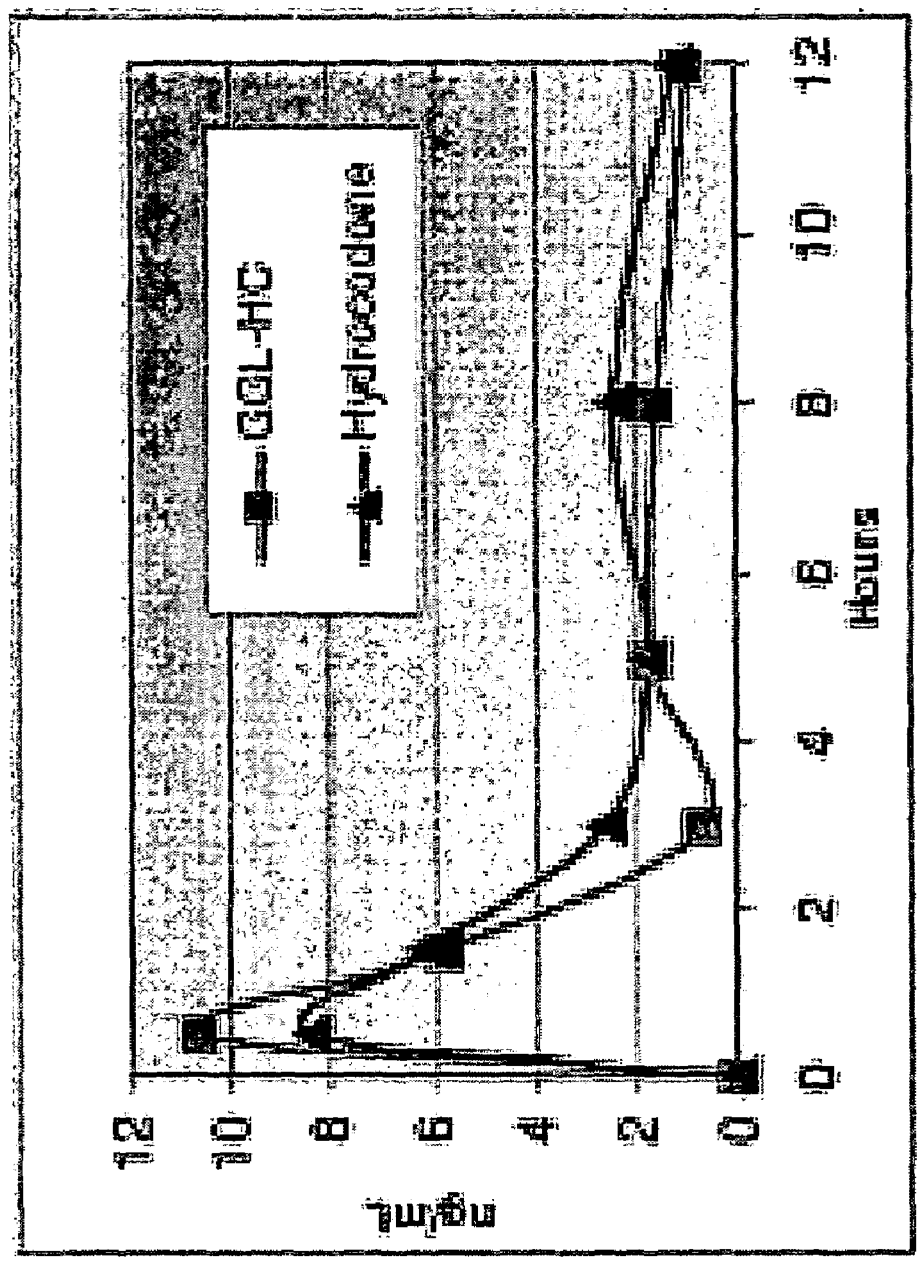
Figure 12:
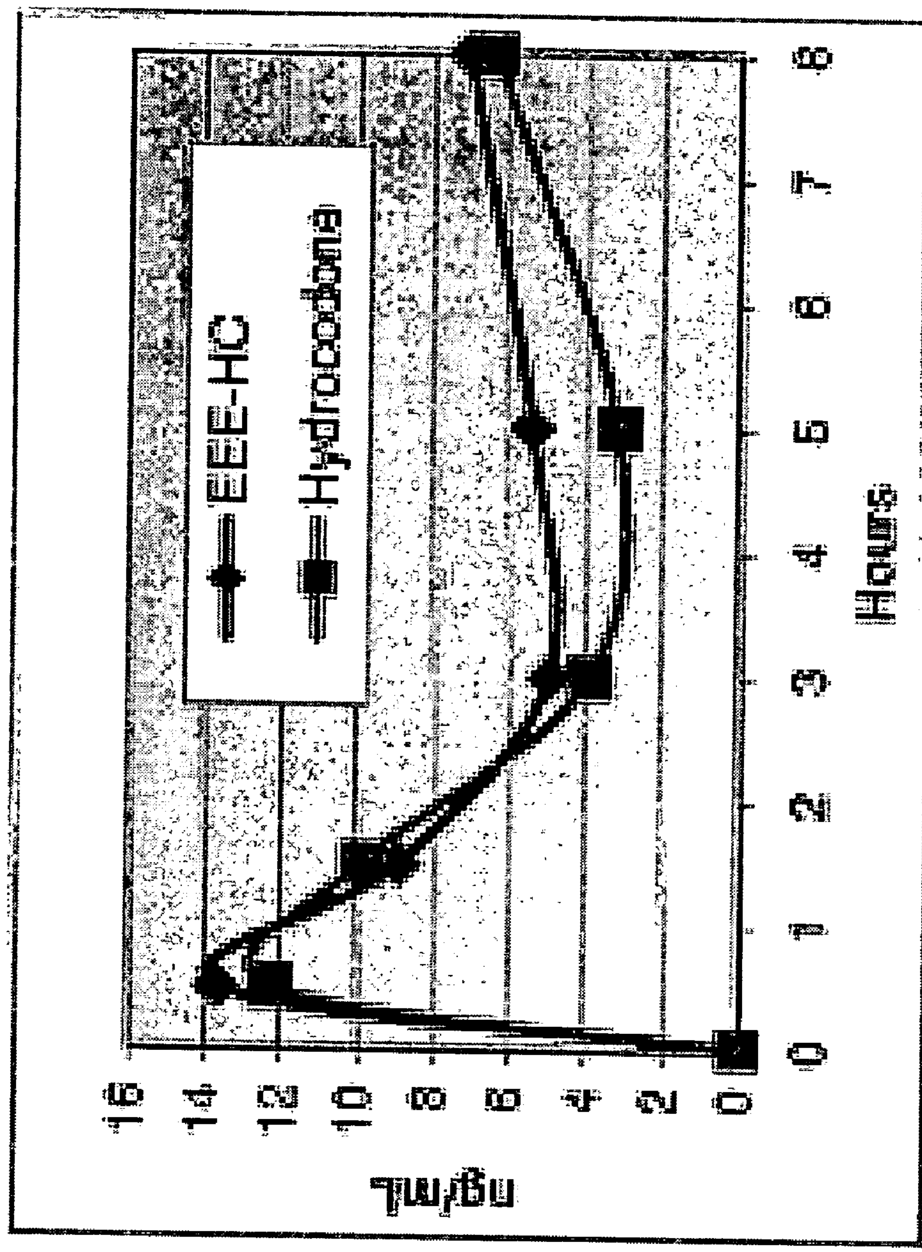
Figure 13:
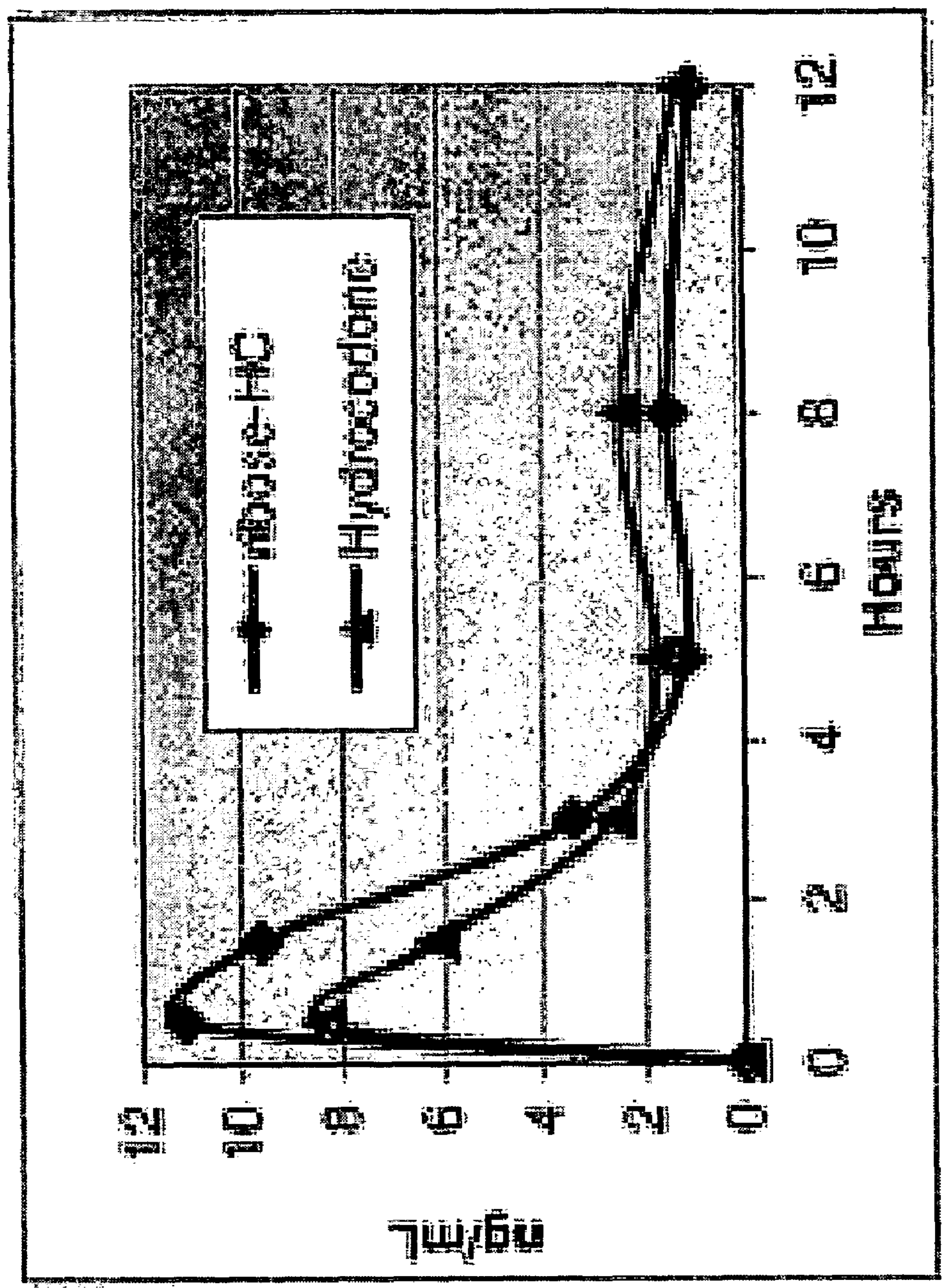
Figure 14:
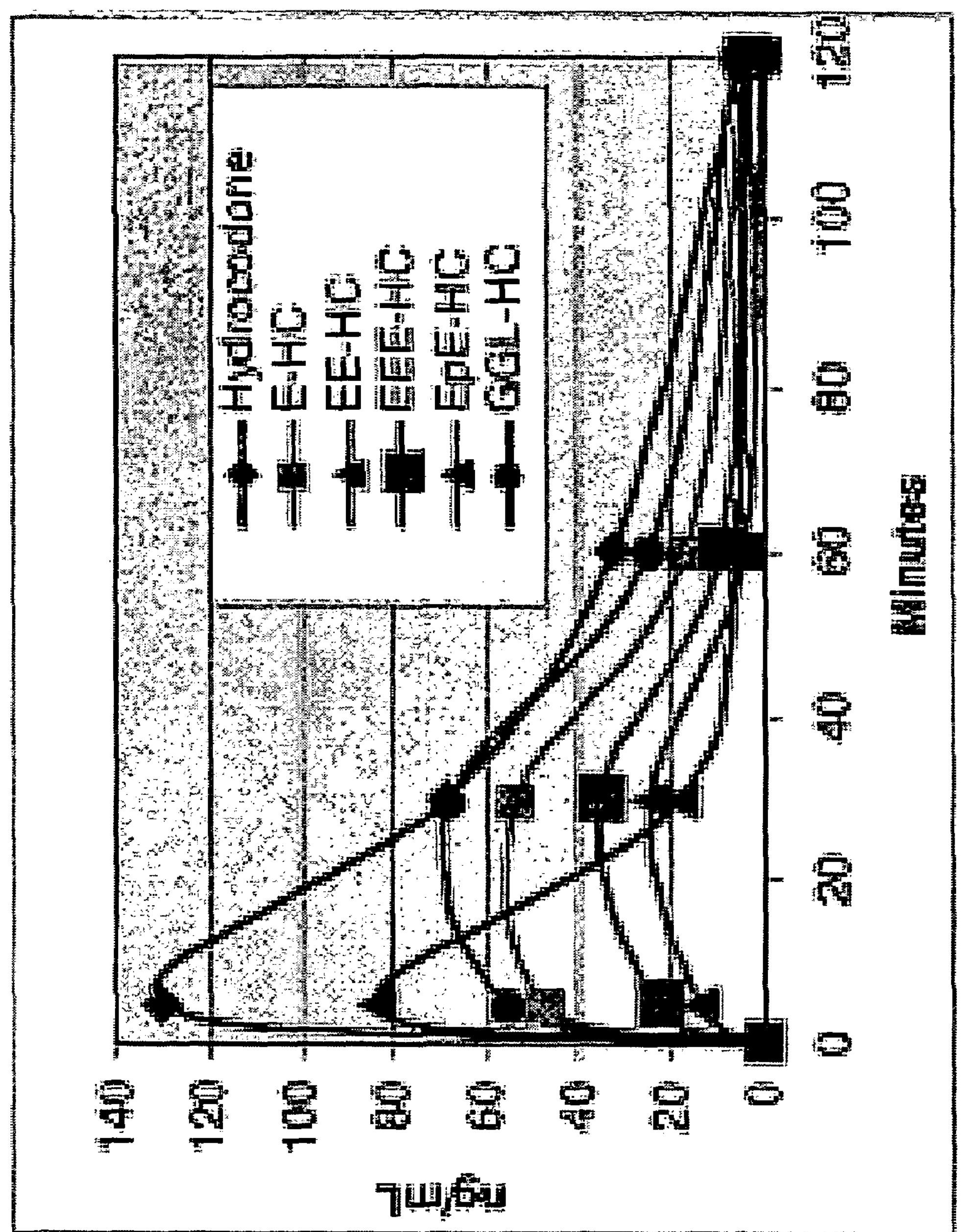
Figure 15:
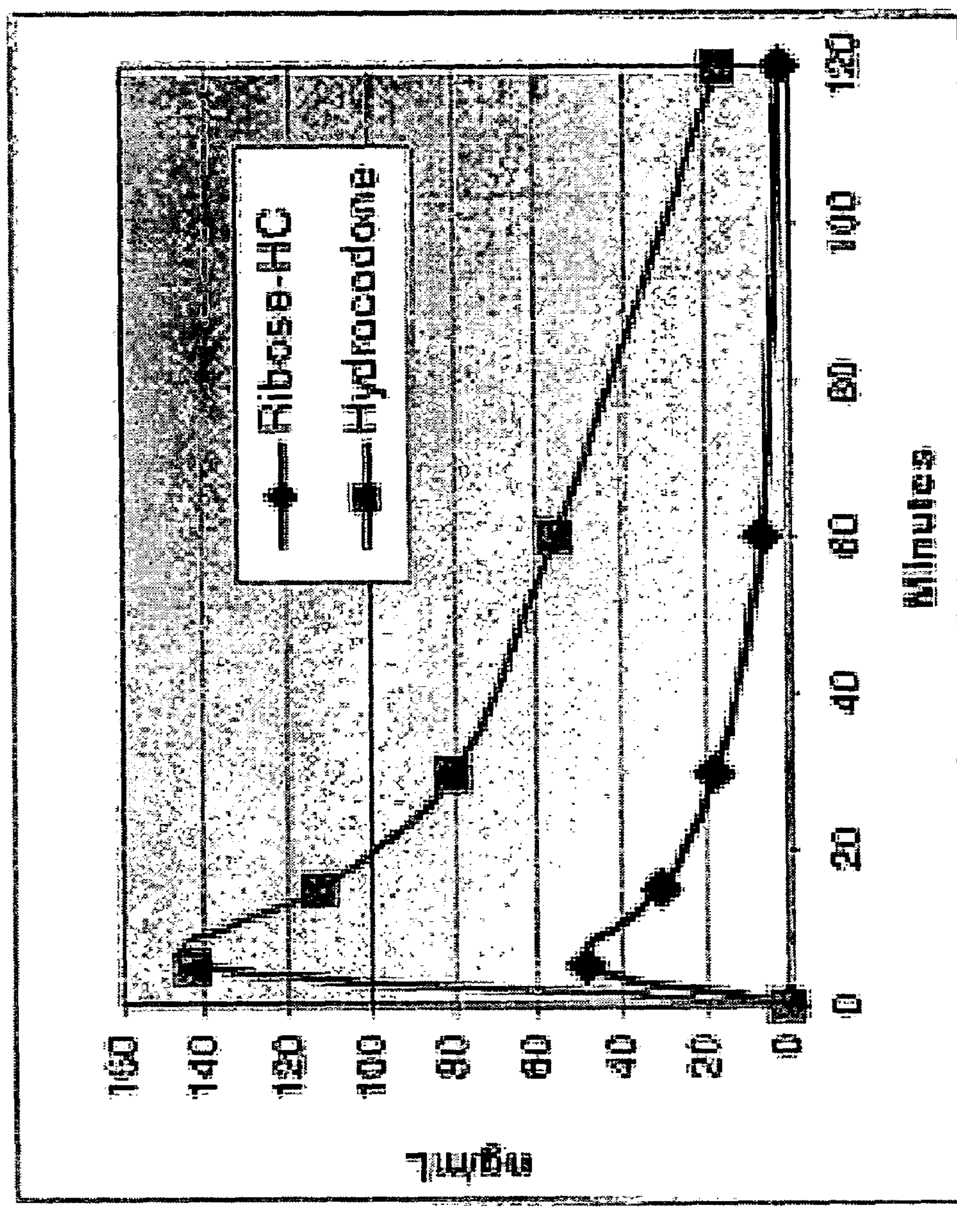
Figure 16:
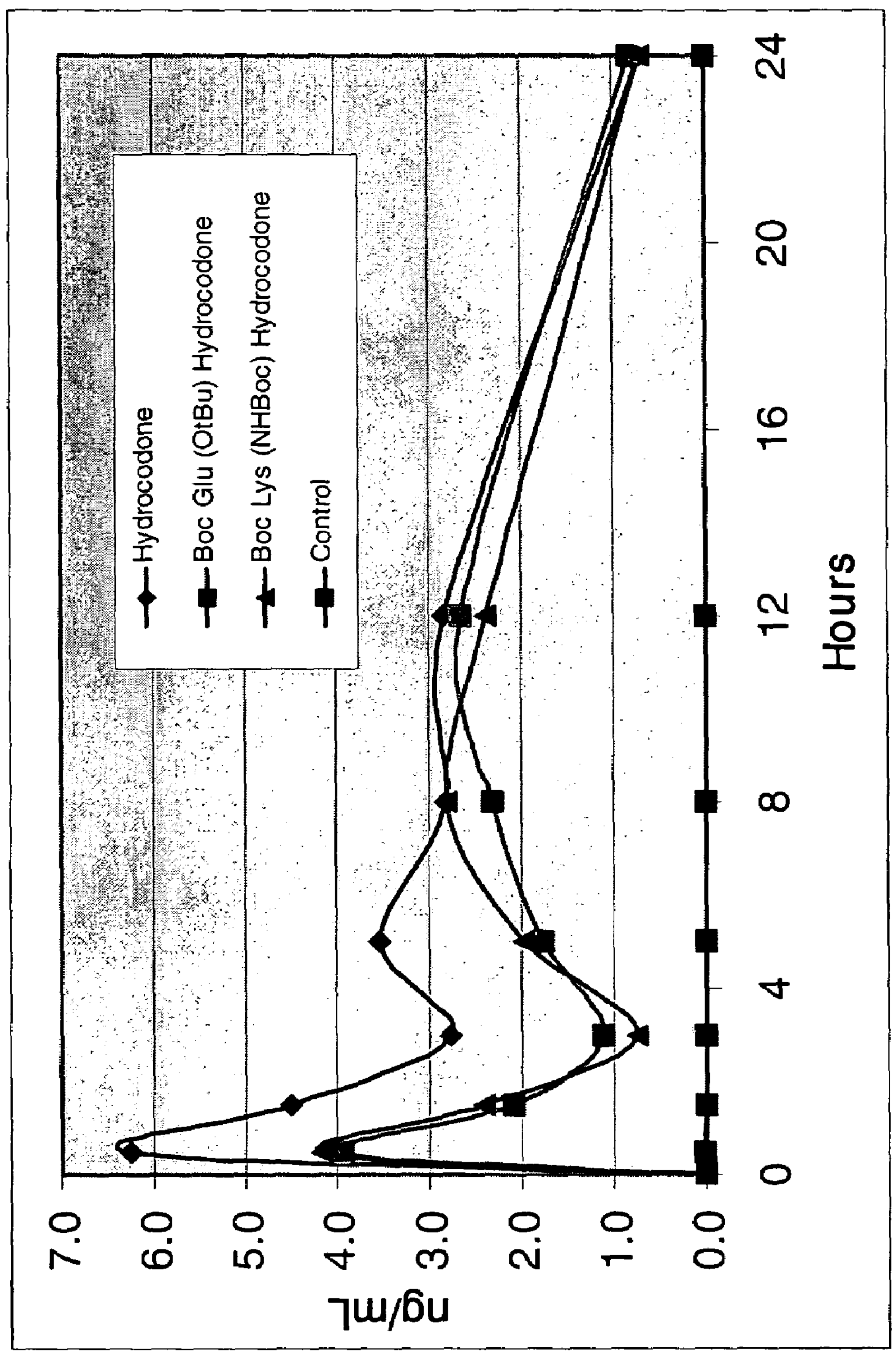
Figure 18:
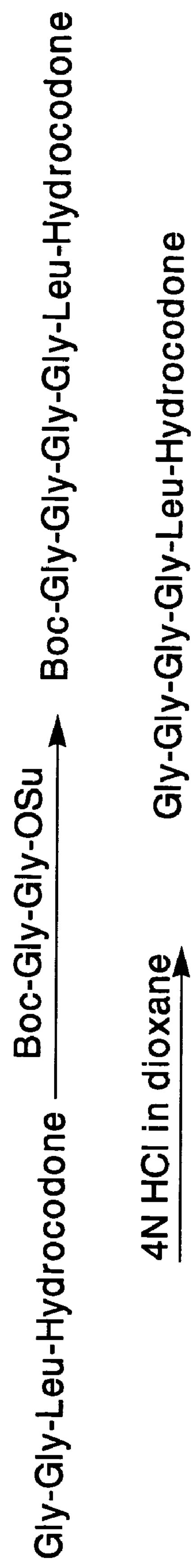
Figure 19:
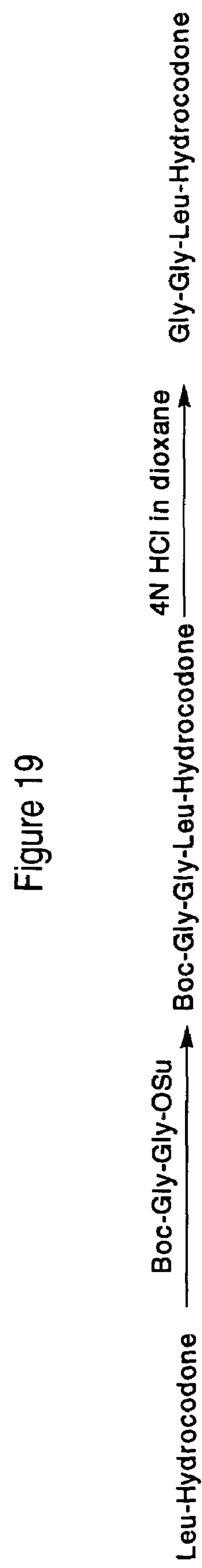
Figure 20:
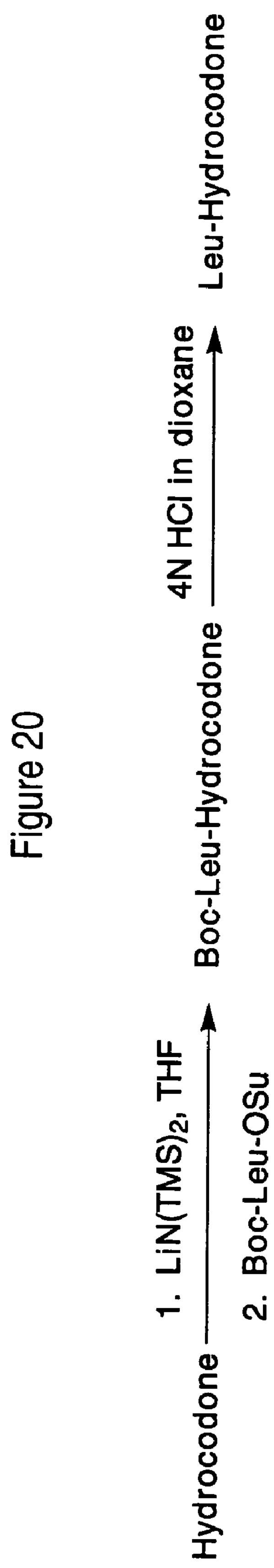
Figure 21:
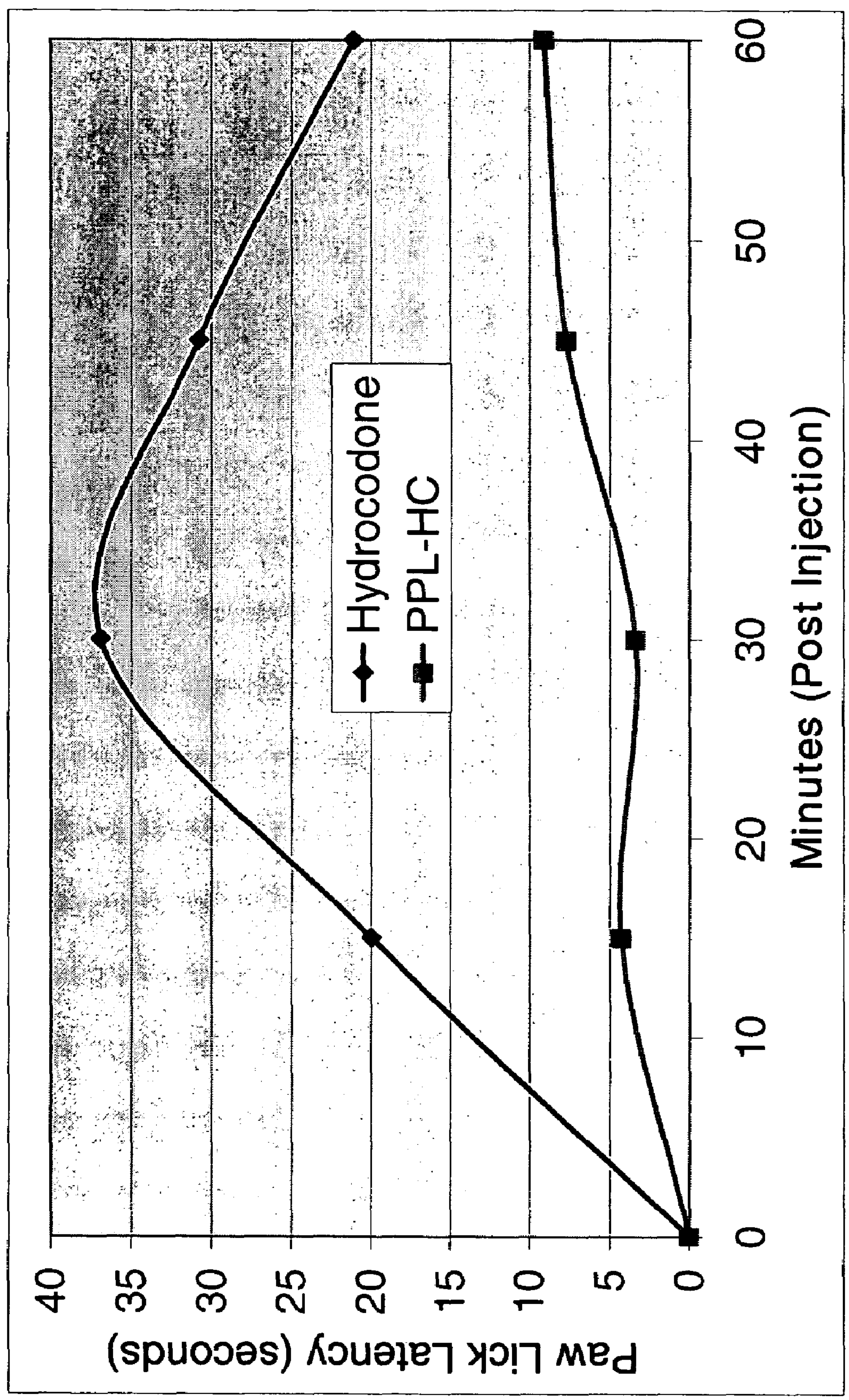
Figure 22:
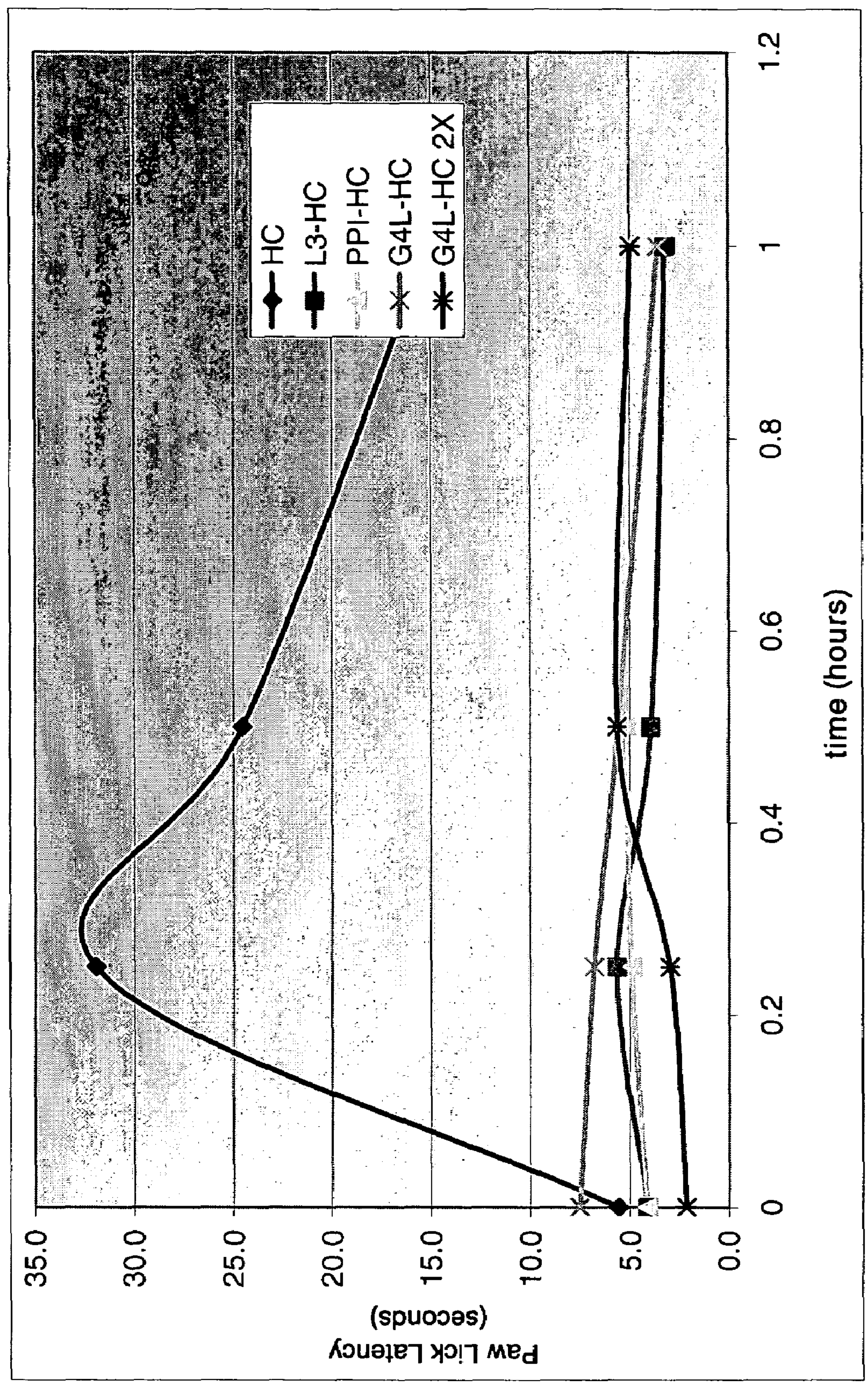

FIG. 9. illustrates Amphetamine vs. Glu-Amphetamine conjugate serum concentration curves;

FIG. 10. Serum concentration curves of peptide-amphetamine conjugates vs. amphetamine;

FIG. 11. illustrates Hydrocodone v. GGL-Hydrocodone conjugate serum concentration curves;

FIG. 12. illustrates Hydrocodone v. EEE-Hydrocodone conjugate serum concentration curves;

FIG. 13. illustrates Hydrocodone v. ribose-Hydrocodone conjugate serum concentration curves;

FIG. 14. illustrates Hydrocodone v. E-Hydrocodone v. EE-Hydrocodone v. EEE-Hydrocodone v. EpE-Hydrocodone v. GGL-Hydrocodone conjugate serum concentration curves;

FIG. 15. illustrates Hydrocodone v. ribose-Hydrocodone conjugate serum concentration curves;

FIG. 16. illustrates Hydrocodone vs. Butylated Amino Acid/Hydrocodone Conjugates Serum Concentration Curves;

Figure 17:
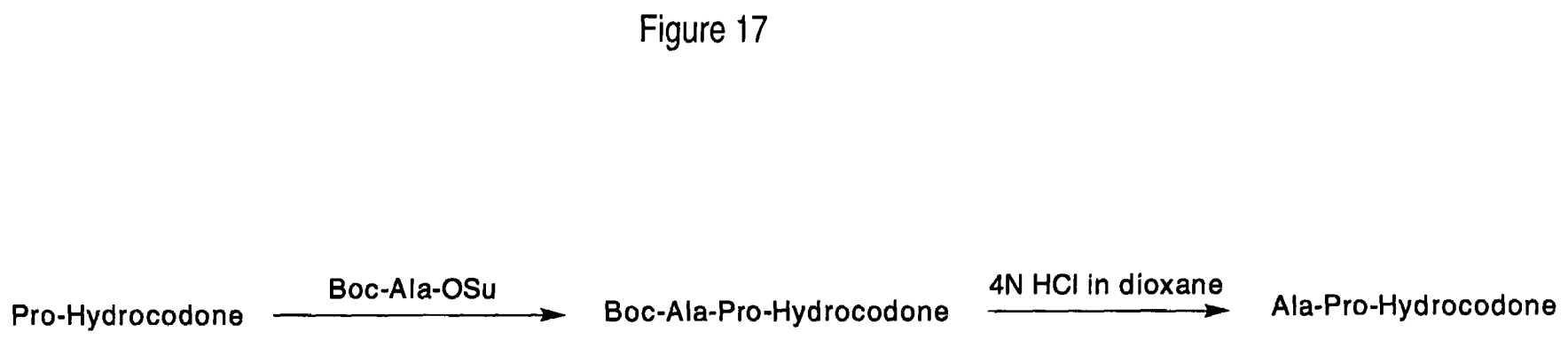

FIG. 17. illustrates preparation of Ala-Pro-Hydrocodone;

FIG. 18. illustrates preparation of Gly-Gly-Gly-Gly-Leu-Hydrocodone;

FIG. 19. illustrates preparation of Gly-Gly-Leu-Hydrocodone;

FIG. 20. illustrates preparation of Leu-Hydrocodone;

FIG. 21. illustrates Paw Lick Latency vs. Time of ProPro-Leu-HC and Hydrocodone; and FIG. 22. illustrates Paw Lick Latency vs. Time of LeuLeuLeu-HC v. ProProIle-HC v. GlyGlyGlyGlyLeu-HC (SEQ ID NO: 1) v. GlyGlyGlyGlyLeu-HC(2×) (SEQ ID NO: 1) v. Hydrocodone.

DETAILED DESCRIPTION

The present invention provides methods for altering controlled substances in a manner that decreases their potential for abuse. The novel compounds may be combined in tablets with suitable excipients or formulated in solution for oral delivery. When delivered by the oral route the controlled substance is released in a time-dependent manner (sustained release) by acid hydrolysis and/or enzymatic cleavage. When administered by injection the controlled substance is released in a time-dependent manner (sustained release) by way of serum enzymes.

Throughout this application the use of "peptide" is meant to include a single amino acid, a dipeptide, a tripeptide, an oligopeptide, a polypeptide, or the carrier peptide. Oligopeptide is meant to include from 2 amino acids to 70 amino acids. Further, at times the invention is described as being an active agent attached to an amino acid, a dipeptide, a tripeptide, an oligopeptide, or polypeptide to illustrate specific embodiments for the active agent conjugate. Preferred lengths of the conjugates and other preferred embodiments are described herein. In another embodiment the number of amino acids is selected from 1, 2, 3, 4, 5, 6, or 7 amino acids. In another embodiment of the invention the molecular weight of the carrier portion of the conjugate is below about 2,500, more preferably below about 1,000 and most preferably below about 500.

Terms Defined

Controlled substance—a substance subject to federal regulation of its manufacture, sale, or distribution because of the potential for, or proved evidence of, abuse; because of its potential for psychic or physiological dependence; because it constitutes a public health risk; because of the scientific evidence of its pharmacologic effect; or because of its role as a precursor of other controlled substances.

Chemical moiety—a substance made up of chemical elements and characterized by a defined molecular composition. It can exist as a part of the drug conjugate and can be separated from the conjugate. Examples include an amino acid, an oligopeptide or a polypeptide, but may be any number of other substances.

Although the discussion which follows focuses on oral administration of the controlled substance, it will be appreciated that the compositions and methods of the present invention are likewise applicable to injectable administration of the controlled substance.

Covalent attachment of a chemical moiety to a controlled substance can render the substance pharmacologically inactive and resistant to absorption. Removal of the chemical moiety by enzymatic or chemical means, however, can restore the activity and the ability to be absorbed. The acidic conditions of the stomach and/or the enzymatic activity present in the gastrointestinal tract can therefore affect release of the active controlled substance. Provided release does not occur too rapidly, the pharmacologically active agent will be absorbed into the bloodstream by a time-release mechanism following oral administration.

One aim of the invention is to decrease potential for abuse by establishing oral extended release via covalent modification. Although this would theoretically decrease the potential for abuse, ideally it would probably only decrease the potential by approximately half for oral administration. For example, equal AUC with a blunted curve ($C_{max}$—50%) would only decrease the oral abuse potential by half (i.e. two anti-abuse pills would presumably induce approximately the same euphoric effect as one control pill). The DEA reports that abuse started with oral administration ultimately leads to intranasal or intravenous abuse due to tolerance. Once tolerance is established the rush effect sought requires the intranasal or intravenous route.

When abused, controlled substances are typically delivered by means other than the oral route, namely by: i) parenteral injection; ii) intranasal delivery; or iii) inhalation. Administration by these routes results in rapid absorption into the bloodstream and the subsequent "rush" effect sought by the addict. It follows that an opioid conjugate that produces a significantly diminished euphoric effect when given by IN or IV, as compared in relative terms to its analgesic effect by oral administration, is valuable in diminishing its potential for abuse. Thus when given by these routes, the covalently modified compound of the invention (adopted for breakdown in the stomach or intestinal tract) is: i) not exposed to the necessary chemical and/or enzymatic conditions necessary for release of the active agent; or ii) the required activity is not present in sufficient amounts to affect rapid release/absorption. The covalently modified controlled substance, therefore, does not produce the euphoric effect sought by addicts.

While other aspects of the invention, eg. sustained release etc. provide additional benefits to patients a preferred aspect of the invention is the design of an opioid conjugate product that has a reasonable shelf life (shelf safe) which can not be abused through current practices. It is a preferred embodiment of the invention, however, that the opioid conjugate not release the opioid through chemical action prior to administration.

There are a number of mechanisms by which the potential for abuse of an analgesic may be decreased, including:

1. Decrease efficiency of the drugs ability to cross the IN barrier.
2. Decrease efficiency of the drugs ability to cross the blood brain barrier. note: 1 and 2 are likely correlated.
3. Increase in the half-life of a conjugate once it reaches the CSF (provided the conjugate is still effective as an analgesic. note: requires the drug-conjugate reaching the CSF.
4. Decreased conversion of the opioid conjugate to a more active metaboloite (e.g. codeine to morphine conversion).

In the case of opioids it may not be necessary (or even desirable) to have all drug release occur in the intestine. If some, or all, of the drug enters as a conjugate it is still a valuable therapeutic agent provided it can still reach the CSF and has an analgesic effect. In this regard "extended release" (more accurately extended analgesia) may be achieved post absorption. This might be accomplished by: 1) extended serum half-life 2) extended CSF half-life 3) temporal absorption across the blood brain barrier (provided it is eventually converted to parent drug and does not have an adverse effect of its own).

The invention may be comprised of any controlled substance covalently attached to any chemical moiety, such as narcotics. Preferably, the controlled substance is an analgesic or stimulant. Further, the controlled substance is preferably of the group of analgesics comprised of the following: codeine, fentanyl, hydrocodone, hydromorphone, levorphanol, methadone, oxymorphone, morphine, oxycodone, propoxyphene, and sufentanyl. The controlled substance may also be amphetamine or methylphenidate. Examples of other controlled drugs include barbiturates, benzodiazepines, skeletal muscle relaxants e.g. meprobamate, and stimulants including amphetamine, methamphetamine, methylphenidate, pemoline, etc.

In a preferred embodiment the invention provides a carrier and active agent which are bound to each other but otherwise unmodified in structure. This embodiment may further be described as the carrier having a free carboxy and/or amine terminal and/or side chain groups other than the location of attachment for the active agent. In a more preferred embodiment the carrier, whether a single amino acid, dipeptide, tripeptide, oligopeptide or polypeptide is comprised only naturally occurring amino acids.

The chemical moiety comprising the invention may be any chemical substance that can be attached to the controlled substance in a manner that renders it pharmacologically inactive. Analgesics and stimulants produce their pharmacological effects through binding to specific receptors or uptake proteins. The attachment of certain chemical moieties can therefore prevent the active substance from binding its receptor(s) or recognition site on its uptake protein. Further, without being bound by theory, the covalent modification is believed to prevent the pharmacological effect by preventing the drug from crossing the blood-brain barrier. Preferably, the attachment of the chemical moiety to the controlled substance will also prevent or substantially delay the absorption of the compound, particularly when the compound is delivered by routes other than oral administration.

Preferably, the attached chemical moiety is an amino acid or more preferably an oligopeptide. The oligopeptide preferably comprises less than 50 amino acids and more preferably less than 6 amino acids. The oligopeptide may comprise (i) a homopolymer of one of the twenty naturally occurring amino acids, (ii) a heteropolymer of two or more naturally occurring amino acids, (iii) a homopolymer of synthetic amino acids or (iv) a heteropolymer of two or more synthetic amino acids or (v) a heteropolymer of one or more naturally occurring amino acids and one or more synthetic amino acids.

The attached chemical moiety may be comprised of other naturally occurring or synthetic substances. Controlled substances, for example, could also be attached to lipids, carbohydrates, nucleic acids; or vitamins. These chemical moieties could be expected to serve the same functions as a polypeptide; namely, effect delayed release in the gastrointestinal tract and prevent rapid absorption of the active agent.

In one embodiment, the covalently attached chemical moiety is removed by the acidic content of the stomach if the controlled substance is attached through an acid labile bond. More preferably, the covalently attached chemical moiety can be removed by enzymatic activity encountered by the compound in the stomach and/or intestinal tract. The stomach and intestinal tract are bathed in degradative enzymes. For example, the pancreas releases into the small intestine a myriad of hydrolytic enzymes such as proteases, lipases, and amylases, and nucleases. Additionally, the intestinal epithelial cells that line the surface of the GI tract produce various surface associated and intracellular degradative enzymes (e.g. brush border peptidases, esterases). These enzymes degrade proteins, lipids, carbohydrates, and nucleic acids contained in ingested food. Thus, it can be expected that the controlled substance will be released from the attached chemical moiety when the appropriate enzyme(s) is encountered in the gastrointestinal tract.

In another embodiment of the invention, the chemical moiety is attached to the controlled substance in a manner in which it is not readily released by conditions found in the mouth (saliva), the intranasal cavity, the surface of the lungs, or in the serum. Extreme acid conditions encountered in the stomach are not present elsewhere in humans. Therefore, any acid dependent release mechanism will occur only after oral administration. Although, degradative enzymes are present in the aforementioned environments, they are not generally present in the high concentrations found in the intestinal tract. Thus, release of the controlled substance by enzymatic cleavage will not occur rapidly when the novel compounds are administered by routes other than oral delivery.

In another embodiment of the invention, the analgesic (e.g. oxycodone or hydrocodone) is attached to a polymer of serine (or other amino acid containing a hydroxyl side chain e.g. threonine, tyrosine) via side chain hydroxyl groups. Alternatively, attachment is to a polymer of glutamic acid through the carboxyl group of the delta carbon of glutamic acid. The resulting ester (carbonate) linkages can be hydrolysed by lipases (esterases) encountered in the small intestine. Esterases are not present at high levels in saliva or on the mucosal surfaces of the nasal cavity, lungs, or oral cavity. Thus, controlled substances attached to polyglutamic acid by this method would not be rapidly released by saliva or when delivered intranasally or by inhalation.

In another embodiment of the invention, the analgesic is attached to an oligopeptide, preferably consisting of between one and five amino acids. In a further embodiment of the invention the amino acids are a heterogenous mixture of the twenty naturally occurring amino acids. Hydrophilic amino acids will tend to prevent passive absorption of the analgesic peptide conjugate through nasal membranes. Thus it is a preferred embodiment of the invention that hydrophilic amino acids be included in the oligopeptide. It is a further preferred embodiment of the invention that lipophilic amino acids be attached closer to the analgesic for optimum stability. Both lipophilic and hydrophilic properties (i.e., amphiphilic) can be satisfied with between three and five amino acids. Thus it is a more preferred embodiment of the invention that the oligopeptide that is attached to the analgesic be an amphiphilic tripeptide.

Preferred amphiphilic amino acids/oligopeptides may be selected from (i) hydrophobic amino acids, preferably in positions next to the active agent to provide increased stability; (ii) amino acid sequences designed to be cleaved by intestinal enzymes (e.g. pepsin, trypsin, chymotrypsin, elastase, carboxypeptidases A and B, etc.) provide for increased bioavailability; (iii) peptides longer than three amino acids for increased stability, increased anti-abuse e.g. less membrane permeability, and potentially more efficient intestinal digestion e.g. major intestinal enzymes target proteins and polypeptides, (iv) or mixtures thereof. In one preferred embodiment the carrier portion of the conjugate is designed for intestinal cleavage.

In a preferred embodiment the cleavage specificity is directed to pepsin and/or chymotrypsin. Examples of preferred carriers include XXXAA or XXAAA, where X is selected from any amino acid, except Arg, Lys, His, Pro, and Met and A is selected from Tyr, Phe, Trp, or Leu. Examples of more preferred carriers are selected from XXXPheLeu wherein X is Glu; XXXPheLeu wherein X is Gly; XXPheLeuLeu wherein X is Glu; and XXPheLeuLeu wherein X is Gly.

In another embodiment the cleavage specificity is directed to trypsin. Examples of preferred carriers include XXXAA or XXAAA wherein X is any amino acid except Pro and Cys and A is Arg or Lys. Examples of more preferred carriers are selected from XXXArgLeu wherein X is Glu; XXXArgLeu wherein X is Gly; XXArgLeuLeu wherein X is Gly; XXX-ArgLeuLeu wherein X is Gly.

The present invention provides covalent attachment of active agents to a peptide. The invention may be distinguished from the above mentioned technologies by virtue of covalently attaching the active agent directly, which includes, for example, pharmaceutical drugs and nutrients, to the N-terminus, the C-terminus or to the side chain of an amino acid, an oligopeptide or a polypeptide, also referred to herein as a carrier peptide.

In another embodiment, the invention provides a composition comprising a peptide and an active agent covalently attached to the peptide. Preferably, the peptide is (i) an oligopeptide, (ii) a homopolymer of one of the twenty naturally occurring amino acids (L or D isomers), or an isomer, analogue, or derivative thereof, (iii) a heteropolymer of two or more naturally occurring amino acids (L or D isomers), or an isomer, analogue, or derivative thereof, (iv) a homopolymer of a synthetic amino acid, (v) a heteropolymer of two or more synthetic amino acids or (vi) a heteropolymer of one or more naturally occurring amino acids and one or more synthetic amino acids.

The invention provides compositions comprising a carrier peptide and an active agent covalently attached to the carrier peptide. Preferably, the carrier peptide is (i) an amino acid, (ii) a dipeptide, (iii) a tripeptide, (iv) an oligopeptide, or (v) polypeptide. The carrier peptide may also be (i) a homopolymer of a naturally occurring amino acids, (ii) a heteropolymer of two or more naturally occurring amino acids, (iii) a homopolymer of a synthetic amino acid, (iv) a heteropolymer of two or more synthetic amino acids, or (v) a heteropolymer of one or more naturally occurring amino acids and one or more synthetic amino acids.

In another embodiment, the invention further provides a composition comprising a single amino acid, a dipeptide or a tripeptide with an active agent covalently attached. Preferably, the amino acid, dipeptide or tripeptide are (i) one of the twenty naturally occurring amino acids (L or D isomers), or an isomer, analogue, or derivative thereof, (ii) two or more naturally occurring amino acids (L or D isomers), or an isomer, analogue, or derivative thereof, (iii) a synthetic amino acid, (iv) two or more synthetic amino acids or (v) one or more naturally occurring amino acids and one or more synthetic amino acids. In another embodiment the amino acids are selected from L-amino acids for digestion by proteases.

In another embodiment, the peptide carrier can be prepared using conventional techniques. A preferred technique is copolymerization of mixtures of amino acid N-carboxyanhydrides. In another embodiment, the peptide can be prepared through a fermentation process of recombinant microorganisms followed by harvesting and purification of the appropriate peptide. Alternatively, if a specific sequence of amino acids is desired, an automated peptide synthesizer can be used to produce a peptide with specific physicochemical properties for specific performance characteristics.

In another embodiment, direct attachment of an active agent to the carrier peptide may not form a stable compound therefore the incorporation of a linker between the active agent and the peptide is required. The linker should have a functional pendant group, such as a carboxylate, an alcohol, thiol, oxime, hydraxone, hydrazide, or an amine group, to covalently attach to the carrier peptide.

In another embodiment, the invention also provides a method for delivering an active agent to a patient, the patient being a human or a non-human animal, comprising administering to the patient a composition comprising a peptide and an active agent covalently attached to the peptide. In a preferred embodiment, the active agent is released from the composition by enzyme catalysis. In another preferred embodiment, the active agent is released in a time-dependent manner based on the pharmacokinetics of the enzyme-catalyzed release.

In another preferred embodiment, the active agent conjugates can incorporate adjuvants such that the compositions are designed to interact with specific receptors so that targeted delivery may be achieved. These compositions provide targeted delivery in all regions of the gut and at specific sites along the intestinal wall. In another preferred embodiment, the active agent is released as the reference active agent from the peptide conjugate prior to entry into a target cell. In another preferred embodiment, the specific amino acid sequences used are not targeted to specific cell receptors or designed for recognition by a specific genetic sequence. In a more preferred embodiment, the peptide carrier is designed for recognition and/or is not recognized by tumor promoting cells.

In another preferred embodiment, the active agent delivery system does not require that the active agent be released within a specific cell or intracellularly. In a preferred embodiment the carrier and/or the conjugate do result is specific recognition in the body. (e.g. by a cancer cell, by primers, for improving chemotactic activity, by sequence for a specific binding cite for serum proteins(e.g. kinins or eicosanoids).

In another embodiment the active agent may be attached to an adjuvant recognized and taken up by an active transporter. In a more preferred example the active transporter is not the bile acid active transporter. In another embodiment, the present invention does not require the attachment of the active agent to an adjuvant recognized and taken up by an active transporter for delivery.

In a preferred embodiments the active agent conjugate is not bound to an immobilized carrier, rather it is designed for transport and transition through the digestive system.

While microsphere/capsules may be used in combination with the compositions of the invention, the compositions are preferably not incorporated with microspheres/capsules and do not require further additives to improve sustained release.

In a preferred embodiment the active agent is not a hormone, glutamine, methotrexate, daunorubicin, a trypsin-kallikrein inhibitor, insulin, calmodulin, calcitonin, L-dopa, interleukins, gonadoliberin, norethindrone, tolmetin, valacyclovir, taxol, or silver sulfadiazine. In a preferred embodiment wherein the active agent is a peptidic active agent it is preferred the active agent is unmodified (e.g. the amino acid structure is not substituted).

In a preferred embodiment the invention provides a carrier and active agent which are bound to each other but otherwise unmodified in structure. In a more preferred embodiment the carrier, whether a single amino acid, dipeptide, tripeptide, oligopeptide or polypeptide is comprises only naturally occurring amino acids.

In a preferred embodiment the carrier is not a protein transporter (e.g. histone, insulin, transferrin, IGF, albumin or prolactin), Ala, Gly, Phe-Gly, or Phe-Phe. In a preferred embodiment the carrier is also preferably not a amino acid copolymerized with a non-amino acid substitute such as PVP, a poly(alkylene oxide) amino acid copolymer, or an alkyloxycarbonyl (polyaspartate/polyglutamate) or an aryloxycarbonylmethyl (polyaspartate/polyglutamate).

In a preferred embodiment neither the carrier or the conjugate are used for assay purification, binding studies or enzyme analysis.

In another embodiment, the carrier peptide allows for multiple active agents to be attached. The conjugates provide the added benefit of allowing multiple attachments not only of active agents, but of active agents in combination with other active agents, or other modified molecules which can further modify delivery, enhance release, targeted delivery, and/or enhance adsorption. In a further embodiment, the conjugates may also be combined with adjuvants or be microencapsulated.

In another preferred embodiment, the composition of the invention is in the form of an ingestible tablet or capsule, an intravenous preparation, an intramuscular preparation, a subcutaneous preparation, a depot implant, a transdermal preparation, an oral suspension, a sublingual preparation, an intranasal preparation, inhalers, or anal suppositories. In another embodiment, the peptide is capable of releasing the active agent from the composition in a pH-dependent manner. In another preferred embodiment the active agent is prepared and/or administered through means other than implantation and/or injectables.

Embodiments of the present invention preferably are not bound to an adjuvant recognized and/or taken up by active transporters. Preferably, the active agent conjugates of the present invention are not attached to active transporters, or antigenic agents such as receptor recognizing sequences found on cells and tumors. Preferably, the active agent conjugate of the present invention is not connected to or constitutes an implantable polymer, which would not biodegrade in less than 48 hours, preferably between 12 and 24 hours. The active agent conjugates of the present invention are preferably designed to release the active agent into the blood, after absorption from the gut, as the reference active agent.

One embodiment of the invention relates to long acting narcotic drugs having significantly reduced abuse potential. The active agent is covalently bound to a peptide/oligopeptide or amino acid, which renders the active agent pharmaceutically inactive until released. Preferably the release mechanism is enzymatic action. Following oral administration the intestinal enzymes release the drug. The enzymatic and/or chemical conditions necessary for the release of the controlled substances is either not present or is minimally active when the drug-peptide conjugate is introduced by inhalation or injection. Thus it is expected that no euphoric effect will occur when the drug-peptide conjugate is inhaled or injected. Further, extending the release of the narcotic prevents spiking of drug levels which provide the desired analgesic effect with a lower or absent euphoria. Controlled substances with these novel properties are less likely to be abused due to the diminished "rush" effect of the modified controlled substance. Consequently, decreasing euphoria while increasing the duration of the analgesic effect enhances and reducing the likelihood of abuse increases the therapeutic value of these pharmaceuticals. The invention also provides for reproducible methods for compositions which are abuse-free for controlled substances, stable under a variety of chemical conditions, reduced euphoric effect and extended absorption into the bloodstream.

The following examples are given by way of illustration and in no way should be construed as limiting as to the full scope of the invention.

EXAMPLES

Example 1

Naltrexone

Naltrexone, an opioid antagonist, was chosen as a model compound for testing conjugates for the hypothesis that conjugates of opioid drugs can afford extended release, while also lowering the potential for abuse. Naltrexone is chemically similar to orally delivered analgesics such as oxycodone and hydromorphone and therefore amenable to synthesizing conjugates for testing in vitro and in vivo performance.

Synthesis

Polyserine-naltrexone (carbonate-linked) conjugates were synthesized by the following method:

1) Polymer activation. N-acetylated polyserine-methyl ester (0.69 g, 7.9 mmol) was dissolved in N-methylpyrolidinone (15 ml) and allowed to stir under argon at ambient temperature. Carbonyldiimmidazole (CDI, 1.93 g, 11.9 mmol) was added and the reaction allowed to stir over night under argon. Then, 100 ml of acetonitrile were added and the mixture allowed to sit at 4° C. for 2 hours. The precipitate that formed was collected by centrifugation and the resulting pellet then resuspended in acetonitrile. This suspension was then centrifuged and the pellet dried over night under a vacuum.

2) Tetrabutylammonium salt of naltrexone. Naltrexone hydrochloride (1.5 g, 3.979 mmol) was dissolved in water (~50 ml) and this solution titrated with 1N LiOH to a pH of ~11-12. Tetrabutylammonium chloride (2.6 g, 4.0 mmol) was then added. The aqueous solution was then extracted with 3 equal volumes of chloroform (20 ml each). The organic solutions were pooled and dried with magnesium sulfate. The solvent was then removed using a rotovap, and the resulting solid dried over night under a high vacuum.

Figure 1:
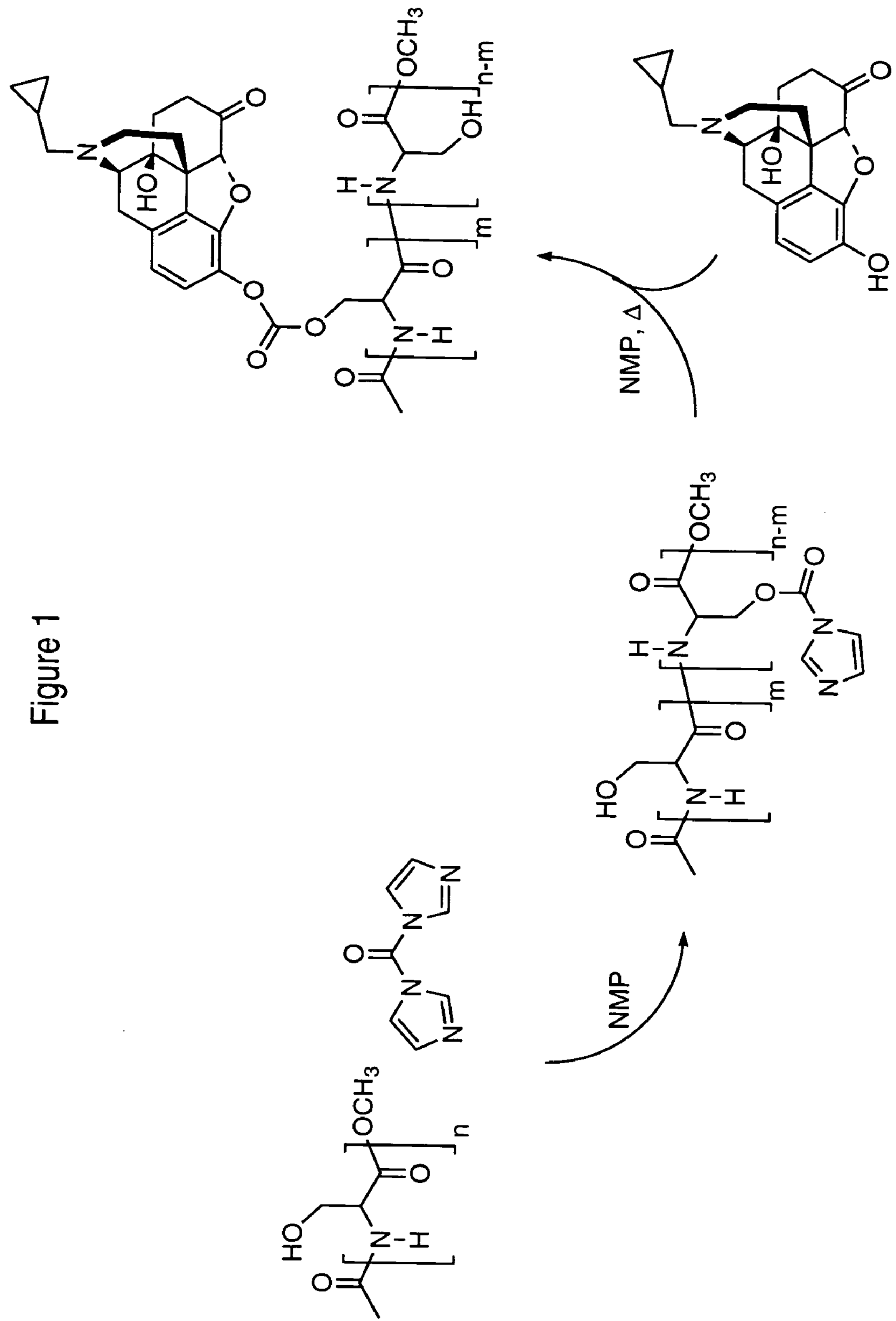
FIG. 1. illustrates the synthesis of polyserine-naltrexone (carbonate-linked) conjugates.

3) Conjugation reaction. The solid material from step 1 was dissolved/suspended in 15 ml of N-methylpyrrolidinone and the resulting solution placed under argon. The naltrexone salt from step 2 was then added, and the reaction then allowed to warm to ~50-60° C. The reaction was then allowed to stir two days under these conditions, at which point water was added (~200 ml). The aqueous solution was then concentrated by ultrafiltration (1000 mw cutoff). The concentrated solution (~5 ml) was then diluted to a volume of 50 ml with water. The aqueous solution was then titrated to pH 3 with 1N HCl and then concentrated by ultrafiltration. This process was repeated two more times. Following the final concentration, the aqueous solution (~5 ml) was then freed of solvent using a rotovap and high vacuum. The resulting solid was then stored over night under high vacuum. This afforded 50 mg of brown solid. A serine:naltrexone ratio of approximately 1:6 (BB272) and 1:10 (BB301) was estimated by nuclear magnetic resonance (NMR). A schematic of synthesis is shown in FIG. 1.

Example 2

In Vivo Performance of Polyserine-naltrexone Conjugate (Rat Model)

Polyserine-naltrexone conjugates were tested in Sprague-dawley rats (~250 g). Defined doses were delivered orally in gelatin capsules containing purified dry powder polyserine-naltrexone conjugates or naltrexone. No excipients were added to the capsules.

Content of naltrexone in the polyserine-naltrexone conjugate BB272 was estimated to be 30% as based on the 1:6 ratio of naltrexone:serine determined by NMR. Polyserine-naltrexone conjugate was given to four rats at a dose of 12 mg which contained 3.6 mg of naltrexone. Doses of naltrexone (3.6 mg) equivalent to the naltrexone content of the conjugate were also given to four rats. Capsules were delivered orally to rats at time-zero using a capsule dosing syringe. Serum was collected from rats 2, 4, 6, 9, and 12 hours after capsule delivery. Serum naltrexone concentrations were determined by ELISA using a commercially available kit (Nalbuphine, product #102819, Neogen Corporation, Lansing Mich.).

TABLE 1

Serum Concentrations (ng/ml) of Individual Rats Fed BB272 Polyserine-naltrexone Conjugate vs. Naltrexone

| | Polyserine-naltrexone | | | | Naltrexone | | | |
|---|---|---|---|---|---|---|---|---|
| Hours | Rat #1 | Rat #2 | Rat #3 | Rat #4 | Rat #1 | Rat #2 | Rat #3 | Rat #4 |
| 2 | 58 | 35 | 22 | 22 | 33 | 91 | 37 | 22 |
| 4 | 66 | 46 | 14 | 27 | 6 | 25 | 12 | 3 |
| 6 | 34 | 21 | 11 | 26 | 13 | 10 | 8 | 6 |
| 9 | 22 | 13 | 4 | 10 | 3 | 6 | 2 | 1 |
| 12 | 8 | 16 | 3 | 5 | 1 | 2 | 1 | 2 |

Figure 2:
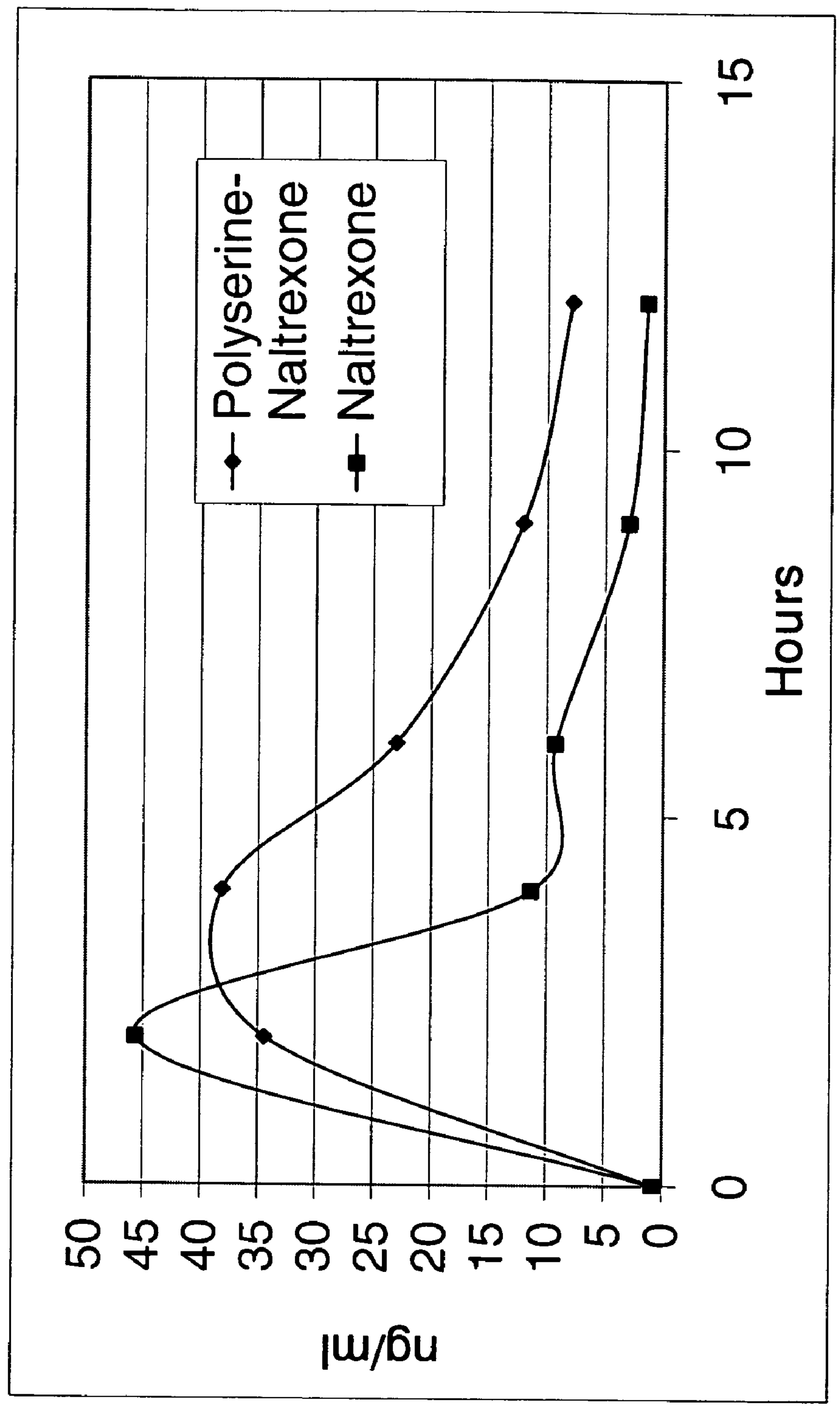
FIG. 2. illustrates mean serum concentration curves of rats orally dosed with BB272 polyserine-naltrexone conjugate vs. naltrexone.

Serum levels of individual animals are shown in Table 1. Mean serum levels are shown in Table 3. (Example 2). As shown in FIG. 2, serum levels spiked earlier for naltrexone (2 hours) than for the drug administered as a polyserine-naltrexone conjugate (4 hours). Serum levels of naltrexone for the polyserine-naltrexone conjugate remained elevated considerably longer than for naltrexone. Additionally, the peak level was significantly lower for the polyserine-naltrexone conjugate. It should be noted that the 2 hour time point was the first measurement of naltrexone serum levels. Since this was the peak level measured for naltexone it can not be determined whether or not levels peaked at a higher concentration earlier. Consequently, it was not possible to accurately determine the $C_{max}$ or area under serum concentration curve (AUC) for naltrexone in this experiment.

Example 3

In Vivo Performance of Polyserine-naltrexone Conjugate

Polyserine-naltrexone conjugates were tested in Sprague-dawley rats (~250 g). Defined doses were delivered orally in gelatin capsules containing purified dry powder polyserine-naltrexone conjugates or naltrexone. No excipients were added to the capsules.

Content of naltrexone in the polyserine-naltrexone conjugate BB272 was estimated to be 30% as based on the 1:6 ratio of naltrexone:serine determined by NMR. Polyserine-naltrexone conjugate was given to five rats at a dose of 12.9 mg which contained 3.6 mg of naltrexone. Doses equivalent to the naltrexone contained in the batch of polyserine-naltrexone (BB 301) were also given to five rats. Additionally, half the equivalent dose (1.8 mg) was given at time-zero, followed by a second half-dose at 6.5 hours to five rats.

Capsules were delivered orally to rats at time-zero using a capsule delivery syringe. Serum was collected at 0.5, 1.5, 3, 5, 8, 12, 15 and 24 hours after capsule delivery for the polyserine-naltrexone (BB301) and equivalent naltrexone dosed rats. Serum was collected at 0.5, 1.5, 3, 5, 8, 11.5, 14.5 and 24 hours after capsule delivery for rats dosed with half-equivalent doses at 0 and 6.5 hours. Serum naltrexone concentrations were determined by ELISA using a commercially available kit (Nalbuphine, product #102819, Neogen Corporation, Lansing Mich.).

TABLE 2

Serum Concentrations (ng/ml) of Individual Rats Fed BB301 Polyserine - naltrexone Conjugate vs. Naltrexone

| | Polyserine-naltrexone | | | | | Naltrexone (equal dose) | | | | |
|---|---|---|---|---|---|---|---|---|---|---|
| Hours | Rat #1 | Rat #2 | Rat #3 | Rat #4 | Rat #5 | Rat #1 | Rat #2 | Rat #3 | Rat #4 | Rat #5 |
| 0.5 | 0 | 0 | 0 | 1 | 0 | 141 | 128 | 126 | 142 | 39 |
| 1.5 | 5 | 4 | 12 | 38 | 23 | 85 | 79 | 46 | 95 | 102 |
| 3 | 21 | 12 | 24 | 16 | 52 | 62 | 44 | 30 | 46 | 91 |
| 5 | 20 | 17 | 23 | 38 | 37 | 193 | 16 | 8 | 19 | 45 |
| 8 | 22 | 14 | 32 | 32 | 13 | 6 | 2 | 5 | 4 | 19 |
| 12 | 10 | 47 | 29 | 19 | 7 | 1 | 2 | 3 | 2 | 3 |
| 15 | 8 | 7 | 13 | 9 | 5 | 1 | 1 | 2 | 2 | 4 |
| 24 | 4 | 4 | 4 | 4 | 3 | 1 | 1 | 3 | 2 | 2 |

TABLE 3

Mean Serum Concentrations of Polyserine-naltrexone BB301 vs. Naltrexone (equal dose) vs. Naltrexone (½ dose X2)

| Hours | Polyserine-naltrexone (ng/ml +/− SD) | Naltrexone (equal) (ng/ml +/− SD) | Naltrexone (½ X2) (ng/ml +/− SD) |
|---|---|---|---|
| 0.5 | 0 | 115 +/− 47 | 72 +/− 69 |
| 1.5 | 17 +/− 14 | 82 +/− 25 | 44 +/− 46 |
| 3 | 25 +/− 16 | 55 +/− 26 | 13 +/− 11 |
| 5 | 27 +/− 10 | 56 +/− 16 | 4 +/− 3 |
| 8 | 23 +/− 9 | 7 +/− 8 | 68 +/− 32 |
| 11.5 | NA | NA | 11 +/− 9 |
| 12 | 22 +/− 16 | 2 +/− 1 | NA |
| 14.5 | NA | NA | 10 +/− 3 |
| 15 | 8 +/− 3 | 2 +/− 1 | NA |
| 24 | 4 +/− 0.4 | 2 +/− 1 | 6 +/− 1 |

Figure 3:
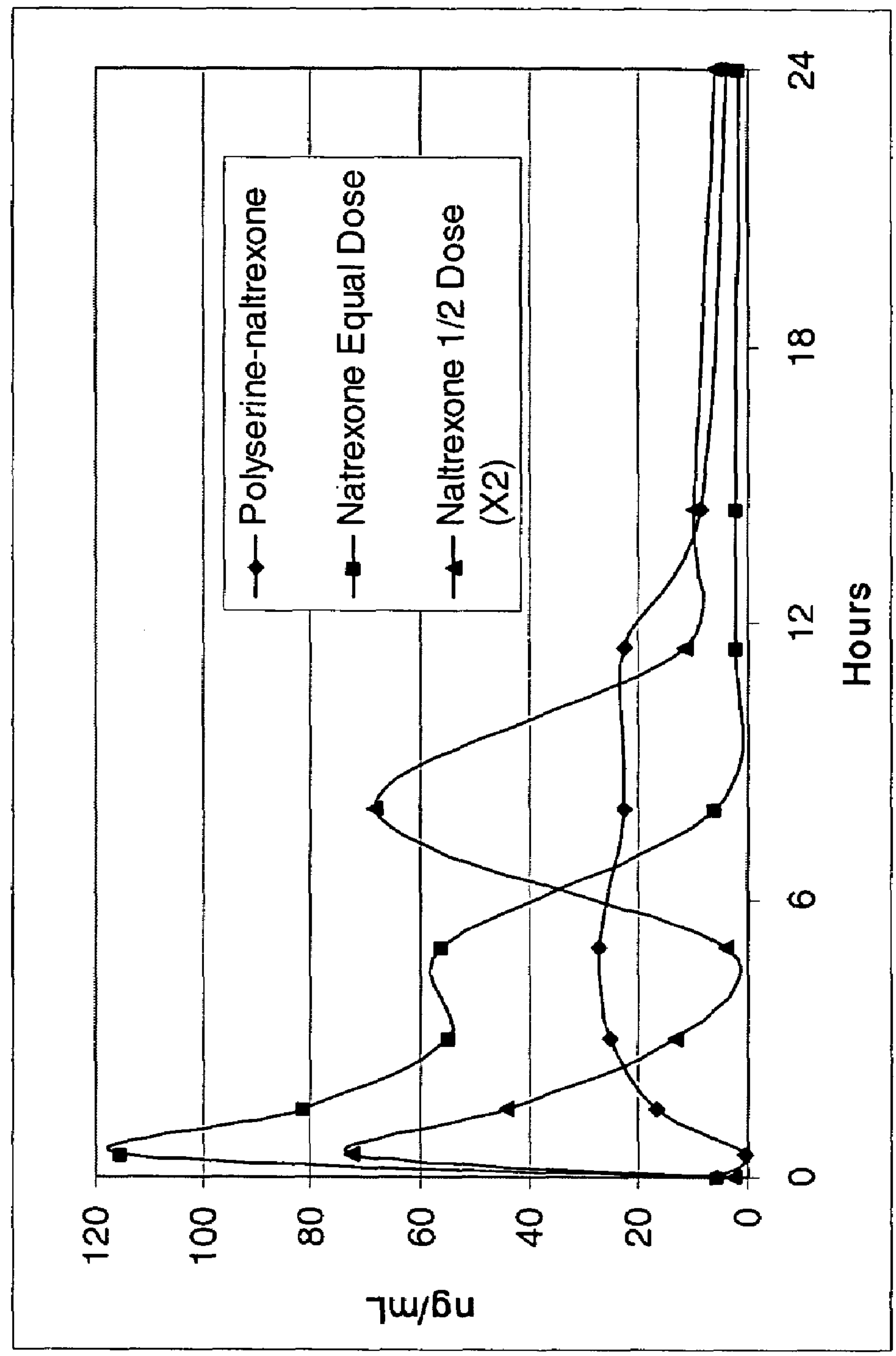
FIG. 3. illustrates mean serum concentration curves of rats orally dosed with BB301polyserine-naltrexone vs. naltrexone (equal dose) vs. naltrexone (½ dose at 0 hours and at 6.5 hours)

Serum levels of individual animals are shown in Table 2. Mean serum levels are shown in Table 3. As shown in FIG. 3, naltrexone serum levels spiked earlier (0.5 hours) for naltrexone than for the drug administed as a polyserine-naltexone conjugate (5 hours). Serum levels of naltrexone for the polyserine-naltrexone conjugate remained elevated considerably longer (>12 hours) than for the monomeric naltrexone control (<8 h). Serum concentration curves crossed at approximately 7 hours. Additionally, the mean of the peak level concentration ($C_{max}$) was significantly lower for the conjugated naltrexone (Table 4). Further, the mean time to peak concentration ($T_{max}$) was significantly longer for the polyserine-naltrexone conjugate (Table 4). The mean AUC of the polyserine-naltrexone conjugate was approximately 75% of the naltrexone mean AUC (Table 4). Statistically the mean AUCs were not significantly different (P<0.05). Serum levels of rats fed one-half-dose (1.8 mg) at time zero and at 6.5 hours were compared to those of rats fed polyserine-naltrexone conjugate. Concentration levels remained elevated for the conjugate past those for the second naltrexone dose, with the curves crossing at approximately 2.5 hours and again at approximately 11 hours (double cross-over of the serum concentration curves).

TABLE 4

Mean Pharmacokinetic Parameters of BB301 Polyserine-naltrexone vs. Naltrexone

| Dosage Form | $C_{max}$ +/− SD (ng/ml) | $T_{max}$ +/− SD (hours) | AUC 0-24 h +/− SD (ng h/ml) |
|---|---|---|---|
| Polyserine-naltrexone | 38.2 +/− 11.9 | 7.3 +/− 3.1 | 356 +/− 66 |
| Naltrexone | 124.5 +/− 16.6 | 0.75 +/− 0.5 | 477 +/− 183 |

Example 4

Synthesis of an Analog of Hydrocodone

Figure 4:
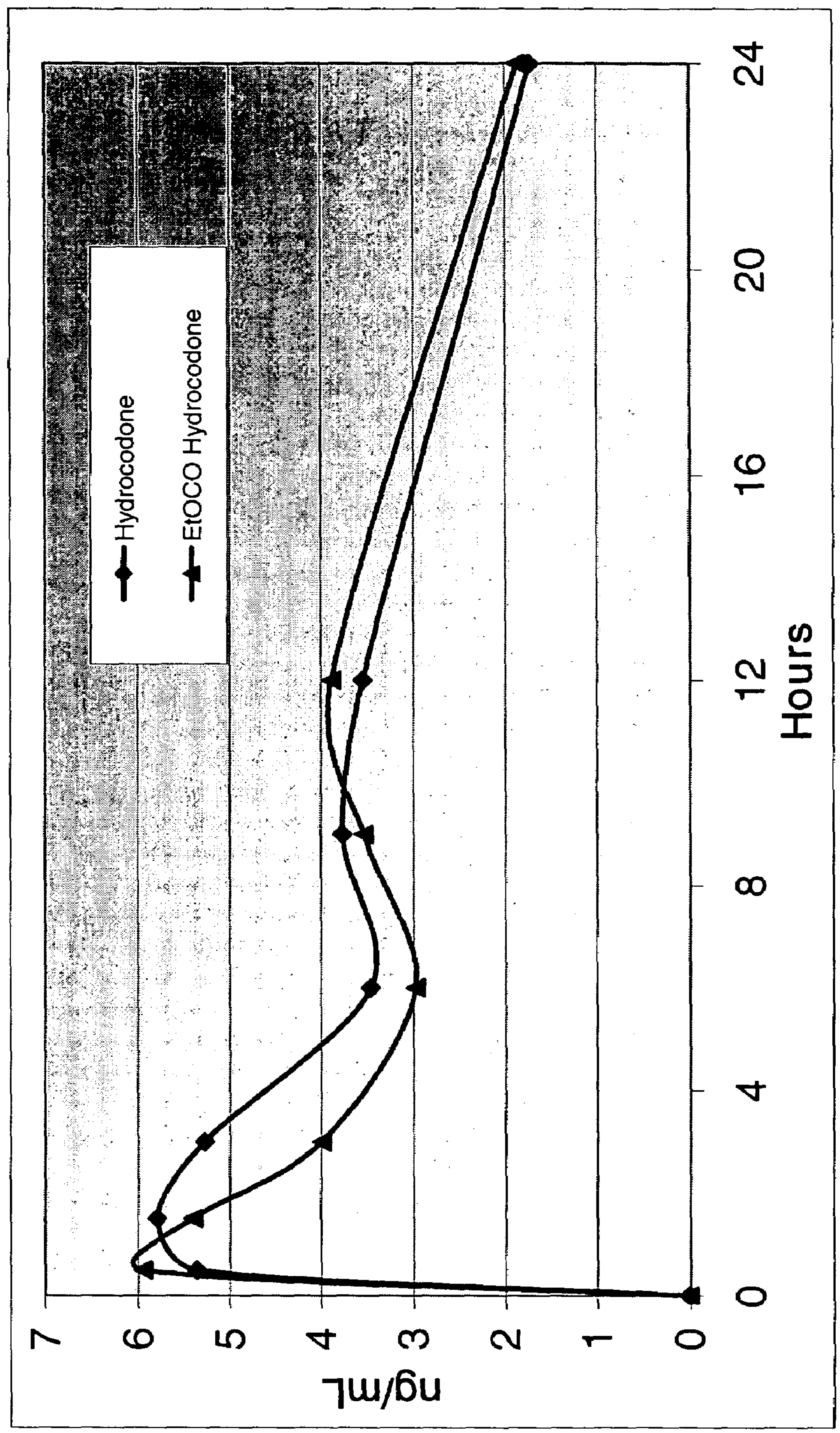
FIG. 4. illustrates Hydrocodone vs. Ethylcarbonate/Hydrocodone conjugates serum concentration curves.

A synthesized analog of hydrocodone, the compound, 6-O-ethoxycarbonyl hydrocodone (EtOCOhydrocodone), was prepared by reaction of the enolate of hydrocodone with ethylchloroformate. The hydrocodone portion was not released under a wide range of pH's and temperatures. EtOCOhydrocodone was studied in a rat model and its pharmacokinetics was nearly identical to that of the reference drug (FIG. 4). Ethoxycarbonylhydrocodone's AUC is 90% of hydrocodone's AUC. EtOCOhydrocodone meets the criteria for an abuse-free narcotic (i.e., stability and in vivo release) when injected.

Figure 5:
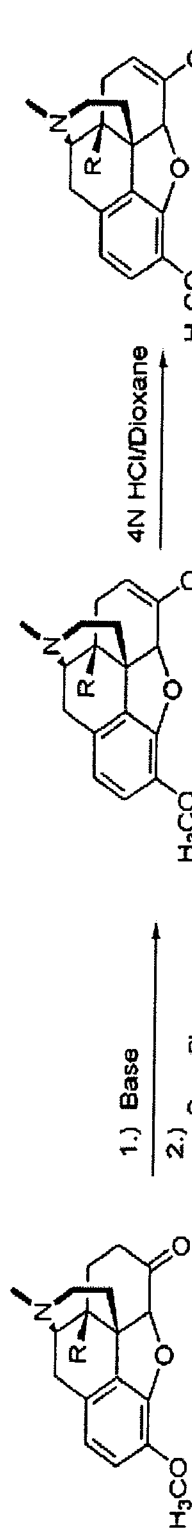
FIG. 5. illustrates how amino acid/narcotic conjugates may be synthesized.
Figure 5:
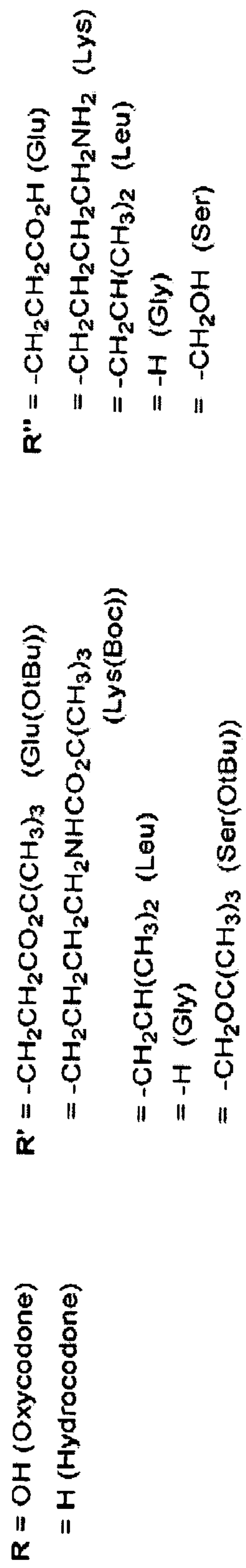
Figure 5:
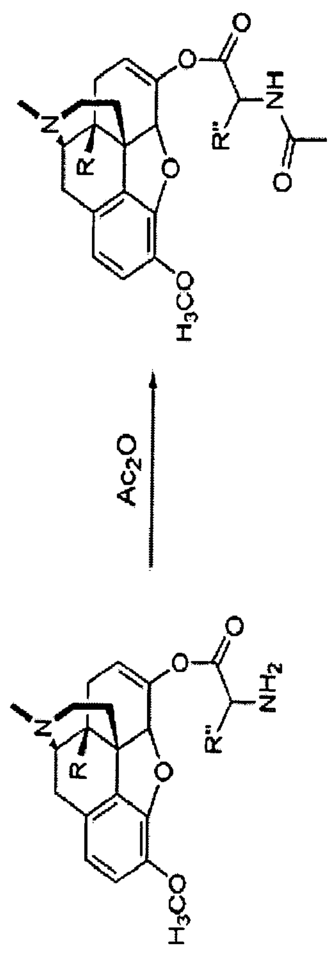
Figure 6:
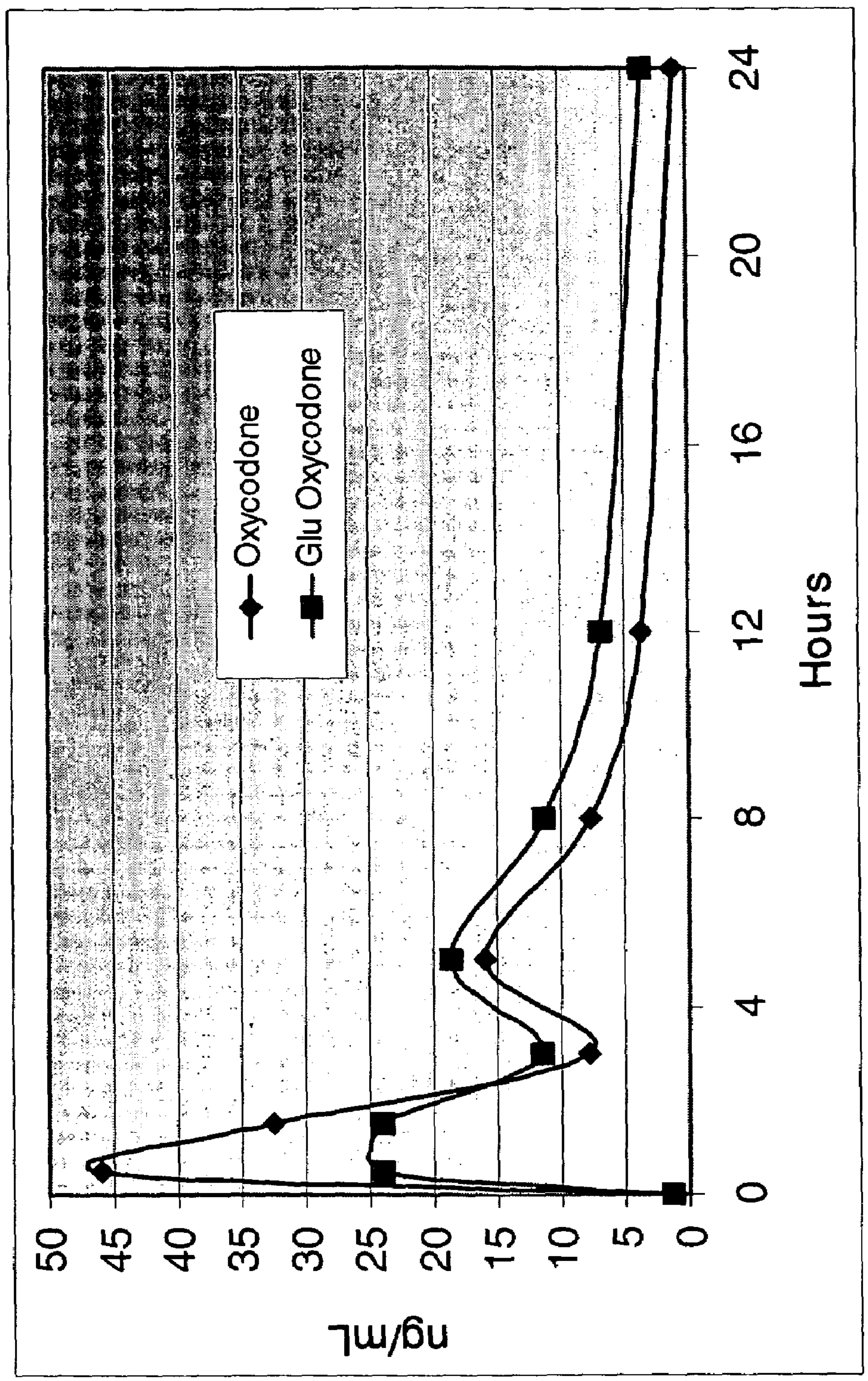
FIG. 6 illustrates Oxycodone vs. Glutamate/Oxycodone conjugate serum concentration curves.
Figure 7:
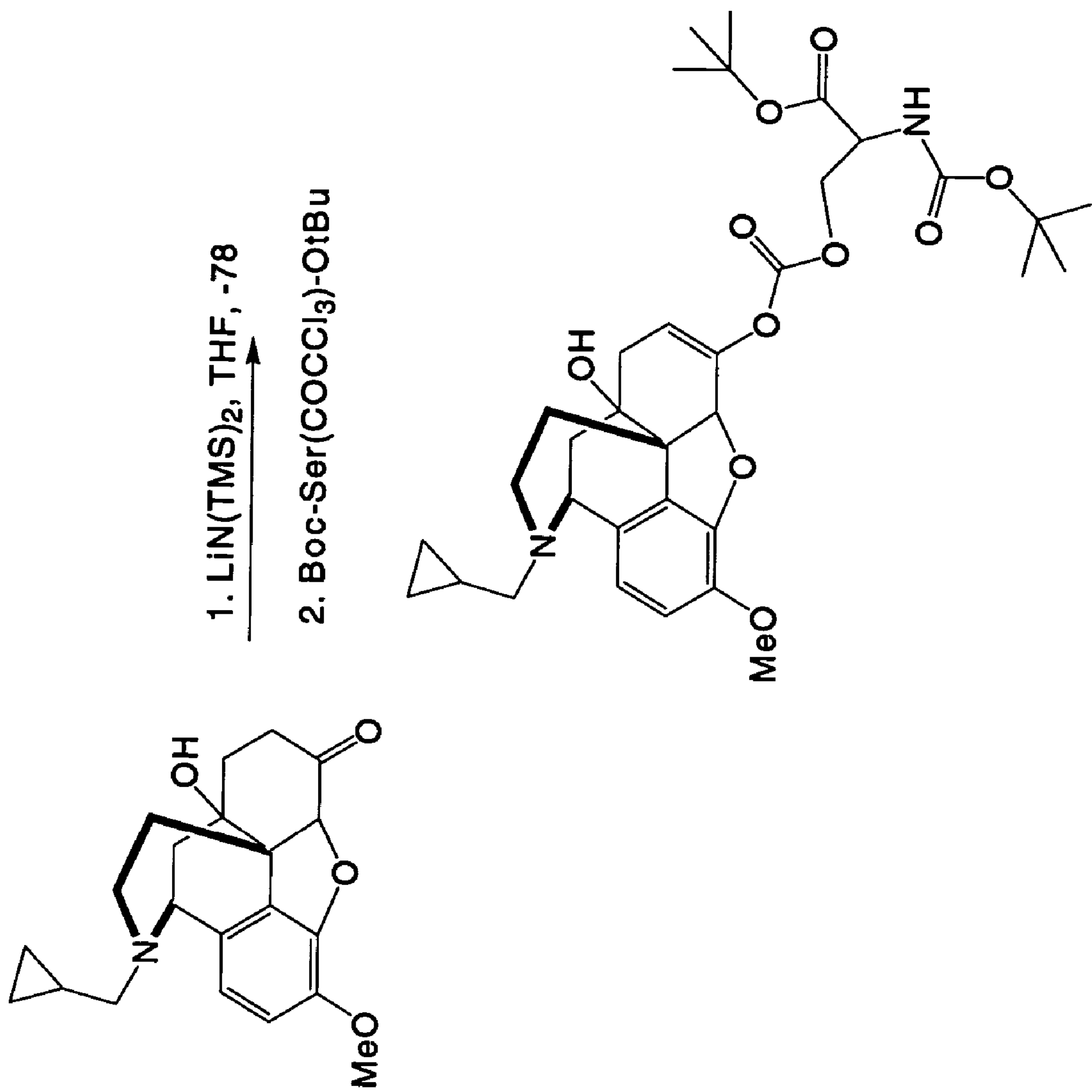
FIG. 7. illustrates the synthesis of a Methylated Opioid conjugate.
Figure 8A:
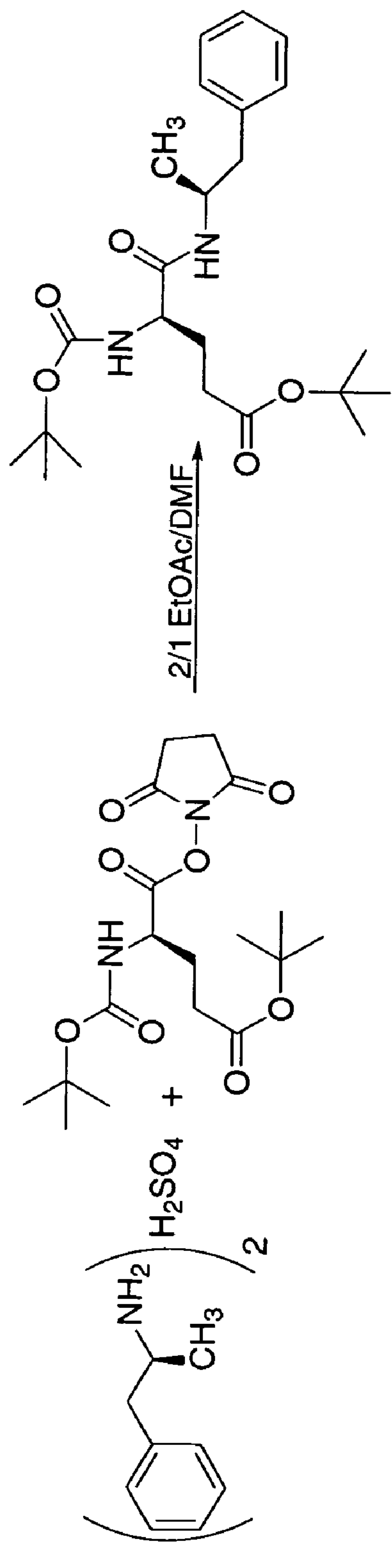
Figure 8B:
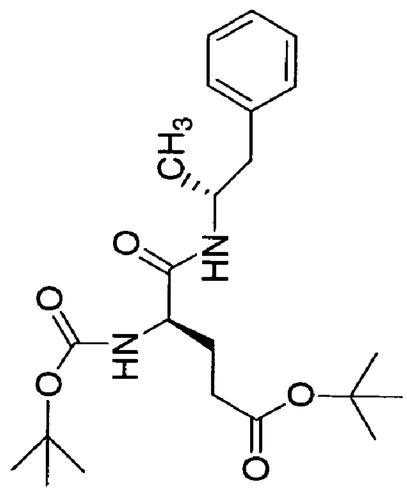
Figure 8B:
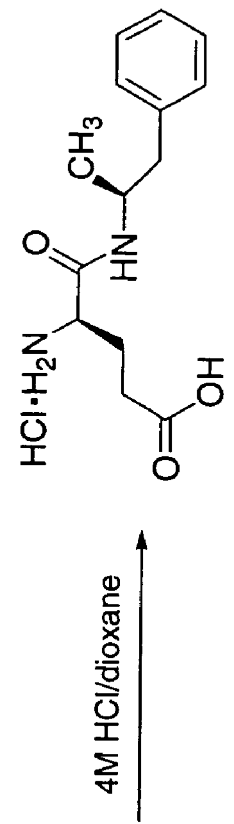

Further, the C-terminus of glutamic acid, leucine, proline, lysine, serine and glycine where attached to the 6-O position of hydrocodone and the C-terminus of glutamic acid to the 6-O position of oxycodone. FIG. 5 shows a general scheme for how amino acid/narcotic conjugates are synthesized using oxycodone and hydrocodone as examples. The anion of oxycodone (or hydrocodone) was reacted with the protected N-hydroxysuccinimide ester (OSu) of the respective amino acid, which is fully deprotected in HCl/dioxane to yield the final product. For example, the enolate of oxycodone is reacted with BocGlu(OtBu)OSu to yield 6-O-BocGlu(OtBu)-oxycodone, which when deprotected gives 6-O,α-glutamyloxycodone. This oxycodone derivative showed similar pharmacokinetics and had 20% greater AUC relative to the parent drug in a rat model. (FIG. 6).

Example 5

Synthesis of Methylated Opioid Conjugates

Boc-Ser(CO-Methyl Naltrexone)-OtBu

To a solution of methyl naltrexone (1.00 g, 2.82 mmol) in THF at −78° C. was added $LiN(SiMe_3)_2$ (1.0M in THF, 5.92 mmol) dropwise via syringe. This solution was stirred at −78° C. for 1 hour. In a separate reaction, Boc-Ser-OtBu (0.220 g, 0.84 mmol) was dissolved in THF (5 ml) with NMM (0.10 ml, 0.92 mmol) and triphosgene (0.250 g, 0.84 mmol) added. This solution was stirred at −78° C. for 30 minutes. The first reaction was added slowly to the second at −78° C. The combined reaction was allowed to warm to ambient temperature and stirred for 18 hours. After this, water (10 ml) was added. Solvent was removed and residue was partitioned between $CHCl_3$/water (50 ml each) and was extracted twice with $CHCl_3$ (50 ml). Combined organics were washed with brine (50 ml), pH 8 water (50 ml), dried with MgSO4 and solvent removed. A preparative TLC was taken (100% CHCl3). NMR of TLC material confirmed the presence of product.

The results of examples 1 through 3 show that conjugation of naltrexone to a polymer of serine via a carbonate linkage can prevent spiking of the drug (decrease $C_{max}$) and afford sustained release (increase $T_{max}$ while maintaining approximately equal AUC). Further, example 4 shows that carbonate linked compounds are substantially resistant to release of naltrexone by exposure to acid, base and protease. Other opioid conjugates can be synthesized in a similar manner to obtain similar characteristics. Example 5 provides an additional method of synthesis by which opioid carbonate conjugates can be synthesized. In particular, this method allows for conjugation to oxycodone via a carbonate linkage.

Example 6

Synthetic Protocol for Amino Acid Conjugate of (S)-amphetamine

Synthesis of Protected Conjugate, Example=BOC-Glu (OtBu)-SAMP The starting material for all these syntheses is dextroamphetamine sulfate which was obtained from Sigma/Aldrich. Since the relative configuration denoted by the term “dextro” may not be relevant to the conjugates, the material is referred to here as the (S)-isomer. This absolute configuration does not change during the reaction sequences.

To a solution of S-amphetamine sulfate (750 mg, 4.07 mmol) in 5 mL of anhydrous DMF stirring at room temperature in an oven-dried 50 mL flask under an Ar atmosphere was added 2.11 mL of diisopropylethylamine (DIPEA, 12.21 mmol). After 5 minutes, BOC-Glu(OtBu)-OSu (1.709 g, 4.07 mmol) in 10 mL of anhydrous EtOAc was added and the mixture was allowed to stir at room temperature overnight. The TLC (9/1 $CHCl_3$/MeOH) indicates that the amphetamine starting material is gone since the UV-active spot on the baseline is no longer present.

The reaction mixture was poured into 30 mL of EtOAc and washed with 2×50 mL of dilute HCl in water (pH 3) and 50 mL of saturated NaCl. After drying over $MgSO_4$, the solution was filtered and the solvent reduced by rotary evaporation. The residue was taken up in a minimum amount of methylene chloride and run through a silica flash column eluting with 50/1 $CH_2Cl_2$/MeOH (adding progressively more MeOH) to 30/1 $CH_2Cl_2$/MeOH. The fast running product was easily separated from the more polar components. After rotary evaporation of the solvent and drying overnight by high vacuum, the purified product (1.625 g, 95%) was ready for the next reaction. The NMR in $CDCl_3$ was consistent with the structure.

Synthesis of Deprotected Conjugate, Example=Glu-SAMP-HCl

A mixture of BOC-Glu(OtBu)-SAMP (1.36 g, 3.23 mmol) and 10 mL of 4M HCl in dioxane was stirred at room temperature in an oven-dried flask under an Ar atmosphere overnight. At this time, the fast-moving protected intermediate was no longer visible on tlc. The solvent was removed by rotary evaporation and the material was dried under high vacuum leaving 886 mg (91%) of the HCl salt. The nmr (dmso-d6) was consistent with the product.

Data from Rat Pharmakinetic Experiments Comparing Amphetamine with Peptide Conjugates Experiments involved male Sprague-Dawley rats (weight 250-300 g) dosed at time zero by oral gavage with a solution of d-amphetamine sulfate (amphetamine) or an equimolar solution of one of the peptide conjugates. Serum samples were obtained by eye bleeds and concentrations determined by ELISA assays. (FIGS. 9 and 10).

Example 7

In Vivo Performance of Amphetamine Conjugates

Pharmacokinetcis by Oral Administration

Peptide-amphetamine conjugates and an equivalent amount of parent amphetamine contained in the conjugate were orally administered separately to male Sprague-Dawley rats (~250 g). Drugs were delivered as oral solutions in water. The amphetamine content of each conjugate was determined by NMR analysis. Serum levels of amphetamine were analyzed by ELISA (Neogene, Lexington, Ky., Amphetamine kit. 109319).

GluGlu-amphetamine and Phe-amphetamine had nearly equal $C_{max}$ and AUC to those of the parent drug (Table 5). The serum concentration curves are shown in FIG. 10. No change in the shape of the curve was observed for the amphetamine conjugates.

TABLE 5

Pharmacokinetic Parameters of Peptide-Amphetamine Conjugates

| Drug | Cmax | Percent Amphetamine | AUC 0-12 h | Percent Amphetamine |
|---|---|---|---|---|
| Amphetamine | 193 +/− 113 | 100 | 530 | 100 |
| GluGlu-Amp | 189 +/− 153 | 98 | 448 | 84 |
| Ser-Amp | 146 +/− 85 | 76 | 290 | 55 |
| Phe-Amp | 175 +/− 77 | 91 | 505 | 95 |

Example 8

In Vivo Performance of Narcotics Conjugates

Pharmacokinetics by Oral Administration

Peptide-narcotic conjugates and an equivalent amount of parent narcotic (hydrocodone or oxycodone) contained in the conjugate were orally administered separately to male Sprague-Dawley rats (~250 g). Drugs were delivered as oral solutions in water or phosphate buffered saline or as solids in gelatin capsules. The narcotic content of each conjugate was determined by HPLC analysis. Serum levels of hydrocodone and oxycodone were analyzed by ELISA (Neogene, Lexington, Ky., Oxymorphone/Oxycodone kit. 102919 and Hydromorphone/Hydrocodone kit. 106610-I).

TABLE 6

In Vivo Performance of Opioid Conjugates Administered Orally

| Compound Class | Compound | Lot Number | Oral Administration - Serum % AUC | % $C_{max}$ | Peak Time | Shape of the Curve |
|---|---|---|---|---|---|---|
| Single AA | Glu-Oxy | TMB12 | 121/110 | 66/55 | 2X/3X | Crossover |
| Single AA | Boc-Lys(Boc)-HC | BB2-102 | 74 | 62 | 1X | No change |
| Single AA | Boc-Glu(OtBu)-HC | BB2-129 | 72 | 67 | 1X | No change |
| Dipeptide | Boc-Glu(OtBu)-Pro-HC | TMB15 | 18 | 31 | 1X | +Clearance |
| Dipeptide | Boc-Glu(OtBu)-Leu-HC | TMB16 | 62 | 64 | 3X | Flat c/out crossover |
| Dipeptide | Boc-Ala-Pro-HC | TMB14 | 60 | 97 | 1X | ++Clearance |
| Dipeptide | Ala-Pro-HC | TMB19 | 48 | 106 | 1X | ++Clearance |
| Dipeptide | Glu-Glu-HC | BB2-121A | 98 | 124 | 1X | No change |
| Tripeptide | GluGluGlu-HC | DL124 | 117 | 111 | 1X | No change |
| Tripeptide | GluGluGlu-HC | DL124 | NA | 314 | NA | Single time point |
| Tripeptide | GluGluGlu-HC | TMB40 | NA | 164 | NA | Single time point |
| Tripeptide | ProProGlu-HC | DL126 | 65 | 66 | 1X | No change |
| Tripeptide | Boc-Gly-Gly-Leu-HC | DL120 | 68 | 96 | 1X | +Clearance |
| Tripeptide | Gly-Gly-Leu-HC | TMB35 | 82 | 126 | 1X | +Clearance |
| Misc. Ester | C8-HC | BB2-97 | 53 | 76 | 1X | +Clearance |
| Carbonate | Ethyl Carbonate-HC | TM302 | 90 | 92 | 1X | No change |
| Carbonate | Galactose-HC | TMB20 | 70 | 61 | 3X | Crossover (barely) |
| Carbonate | Galactose (protected)-HC | TMB18 | 80 | 68 | 3X | Crossover (barely) |
| Carbonate | Ribose-HC | TMB34 | 106 | 132 | 1X | No change |

Oral Bioequivalence

Oral studies are summarized in Table 6. Seventeen narcotic conjugates have been tested for oral bioavailability vs. the parent drug. These include 13 peptide conjugates, 2 monosaccharide conjugates, and 2 lipid conjugates. Eleven of the nine peptide conjugates had 60% or greater bioavailability based on AUC. Examples, which when compared to an equivalent dose of the parent drug, include: Glu-Oxycodone which was 121% bioavailable (FIG. 6); GlyGlyLeu-Hydrocodone which was 82% bioavailable (FIG. 11), and GluGluGlu-HC which was 117% bioavailable (FIG. 12). The Ribose-HC conjugate had 106% when compared to an equivalent dose of the parent drug (FIG. 13).

Oral Kinetics

A sustained release profile was observed with one of the amino acid conjugates Glu-Oxycodone (FIG. 6). The compound showed a blunted curve (decrease in $C_{max}$) combined with a 2-fold increase in time to peak concentration ($T_{max}$) and approximately equivalent AUC. Glu-Oxycodone, however, is not sufficiently stable to warrant consideration as an anti-abuse product. No other narcotics compounds tested to date showed sustained release kinetics with equal AUC. One other compound, protected Glu-Leu-HC, showed an increase in $T_{max}$ without equal AUC.

Pharmacokinetcis by Intranasal Administration

TABLE 7

In Vivo Performance of Opioid Conjugates Administered Intranasally

| Compound Class | Compound | Lot Number | Intranasal Administration - Serum % AUC | % $C_{max}$ | Peak Time | Comments | Buffer |
|---|---|---|---|---|---|---|---|
| Parent Drug | Hydrocodone | NA | 100 | 100 | 1X | Rapid absorption | PBS |
| Single AA | Glu-HC | BB2-131 | 60 | 55 | 6X | Flat curve c/out crossover | PBS |
| Dipeptide | $Glu_{pyro}$-Glu-HC | BB2-132 | 42 | 65 | 1X | Rapid Absorption | PBS |

TABLE 7-continued

In Vivo Performance of Opioid Conjugates Administered Intranasally

| Compound Class | Compound | Lot Number | Intranasal Administration - Serum % AUC | % $C_{max}$ | Peak Time | Comments | Buffer |
|---|---|---|---|---|---|---|---|
| Dipeptide | Glu-Glu-HC | BB2-121A | 23 | 22 | 6X | Flat curve c/out crossover | PBS |
| Tripeptide | Glu-Glu-Glu-HC | DL124 | 36 | 33 | 6X | Flat curve c/out crossover | PBS |
| Tripeptide | Glu-Glu-Glu-HC | TMB40 | 47 | 58 | 1X | No change in curve | PBS |
| Tripeptide | Glu-Glu-Glu-HC | TMB40 | 70 | 88 | 1X | No change in curve | Water |
| Tripeptide | Gly-Gly-Leu-HC | TMB35 | 77 | 62 | 6X | Flat curve c/out crossover | PBS |
| Carbonate | Ethyl Carbonate-HC | TM302 | 150 | 145 | 1X | Rapid absorption | PBS |
| Carbonate | Galactose-HC | TMB20 | 83 | 86 | 1X | Rapid absorption | PBS |
| Carbonate | Ribose-HC | TMB34 | 20 | 34 | 1X | No change in curve | PBS |

Intranasal Bioavailability

Intranasal (IN) studies are summarized in Table 7. All peptide conjugates tested thus far had decreased absorption by the intranasal route. Preliminary data suggests that inhibition of absorption is correlated with 1) length of peptide, 2) polarity, and 3) charge. GluGlu-HC and GluGluGlu-HC were inhibited more than Glu-HC. A relatively lipophilic tripeptide GlyGlyLeu was not inhibited as much as the more polar tripeptide GluGluGlu-HC. GlupyroGlu-HC was absorbed more rapidly that GluGlu-HC, which has a greater net (negative) charge (FIG. 14).

The IN absorption of Ribose-HC (FIG. 15) was significantly inhibited (approximately 80%). This particular compound still contained small amounts of free hydrocodone; therefore, inhibition of absorption may have been essentially complete.

The IN model was used to test the absorption of EEE-HC in water and in saline (PBS, pH 7.4). The inhibition of IN absorption was more significantly inhibited in PBS than in water. Therefore other compounds should be tested in the IN model in water and perhaps other buffers.

Example 9

Stability of Narcotic Conjugates

It is also possible to further stabilize any unstable conjugates by tethering to a larger peptide. To illustrate this point, the synthetic precursors, 6-O-BocGlu(OtBu)hydrocodone and 6-O-BocLys(NHBoc)-hydrocodone, which are completely stable in water at room temperature and under heated conditions as shown in Table 8 and Table 9. The conjugates are also stable at a wide range of pH's.

TABLE 8

Hydrolysis rate of Amino Acid/Narcotic conjugates in water

| Amino Acid/Narcotic Conjugate | % Release of Narcotic in Water (neutral pH) 0 Hours | 1 Hour | 6 Hours | 24 Hours |
|---|---|---|---|---|
| 6-O-Glu-Hydrocodone | 0 | 4 | 19 | 42 |
| 6-O-Gly-Hydrocodone | 6 | 8 | 11 | 32 |
| 6-O-Pro-Hydrocodone | 4 | 11 | 25 | 71 |
| 6-O-Glu-Oxycodone | 3 | 5 | 22 | 55 |

TABLE 9

Stability of Opioid Conjugates

| Compound Class | Compound | Lot Number | abuse resistance tests H2O (24 h, RT) | H2O (1 h, 90 C.) |
|---|---|---|---|---|
| Single AA | Ser-HC | TMB10 | 45 | 98 |
| Single AA | Glu-Oxy | TMB12 | 55 | n/a |
| Single AA | Glu-HC | BB2-131(99) | 79 | 100 |
| Single AA | Gly-HC | TM304f | 26 | 63 |
| Single AA | Pro-HC | TMB9 | 71 | 97 |
| Single AA | Phe-HC | BB2-158 | | 54 |
| Single AA | Leu-HC | CM171 | 10 | 49 |
| Single AA | Ile-HC | BB2-154 | 16 | 46 |
| Single AA | Aib-HC | BB2-153 | 0 | 45 |
| Dipeptide | Ala-Pro-HC | TMB19 | 100 | 100 |
| Dipeptide | $Glu_{pyro}$-Glu-HC | BB2-132 | 11 | 50 |
| Dipeptide | Glu-Glu-HC | BB2-121A | 45 | n/a |
| Tripeptide | Gly-Gly-Leu-HC | TMB35 | 5 | 16 |
| Tripeptide | Gly-Gly-Glu-HC | BB2-147 | 13 | 97 |
| Tripeptide | Gly-Gly-Ile-HC | BB2-163 | | 0 |
| Tripeptide | Gly-Gly-Phe-HC | | | |
| Tripeptide | Gly-Gly-Aib-HC | BB2-160 | | 9 |
| Tripeptide | Gly-Leu-Ile-HC | | | |
| Tripeptide | Gly-Phe-Ile-HC | | | |
| Tripeptide | Gly-Leu-Leu-HC | | | |
| Tripeptide | Gly-Phe-Leu-HC | | | |

TABLE 9-continued

Stability of Opioid Conjugates

| Compound Class | Compound | Lot Number | abuse resistance tests H2O (24 h, RT) | H2O (1 h, 90 C.) |
|---|---|---|---|---|
| Tripeptide | Leu-Pro-Glu-HC | DL125 | 3 | 65 |
| Tripeptide | Leu-Pro-Leu-HC | DL127 | 0 | 2 |
| Tripeptide | Leu-Pro-Phe-HC | | | |
| Tripeptide | Pro-Pro-Glu-HC | DL126 | 1 | 51 |
| Tripeptide | Pro-Pro-Leu-HC | DL128 | 0 | 1 |
| Tripeptide | Pro-Pro-Ile-HC | BB2-165 | | 0 |
| Tripeptide | Pro-Pro-Phe-HC | | | |
| Tripeptide | Glu-Glu-Glu-HC | DL124 | 19 | 61 |
| Tripeptide | Leu-Leu-Glu-HC | | | |
| Tripeptide | Leu-Leu-Leu-HC | | | |
| Pentapeptide | Glu5-HC (SEQ ID NO: 2) | DL1-147 | | 53 |
| Pentapeptide | Gly4-Leu-HC (SEQ ID NO: 1) | | | |
| Pentapeptide | Gly4-Ile-HC (SEQ ID NO: 3) | | | |
| Pentapeptide | Gly4-Aib-HC (SEQ ID NO: 4) | | | |
| Pentapeptide | Gly4-Phe-HC (SEQ ID NO: 5) | | | |
| Pentapeptide | Gly2-Glu3-HC (SEQ ID NO: 6) | | | |
| Pentapeptide | Glu2-Gly2-Aib-HC (SEQ ID NO: 7) | | | |
| Pentapeptide | Glu2-Gly2-Leu-HC (SEQ ID NO: 8) | | | |
| Pentapeptide | Glu2-Gly2-Ile-HC (SEQ ID NO: 9) | | | |
| Pentapeptide | | | | |
| Pentapeptide | | | | |
| Pentapeptide | | | | |
| Misc. Ester | C18-HC | TM301 | 0 | |
| Misc. Ester | C8-HC | BB2-97 | 0* | |
| Carbonate | Ethyl Carbonate-HC | TM302 | 0 | |
| Carbonate | Galactose-HC | TMB20 | 7 | |
| Carbonate | Galactose(protected)-HC | TMB18 | 0* | |
| Carbonate | Ribose(protected)-HC | TMB28 | n/a | n/a |
| Carbonate | Ribose-HC | TMB34 | 4 | |

numbers based upon narcotic release
*poor solubility in H2O

The protected amino acid-hydrocodone compounds were tested in a typical rat model. Biphasic absorption of hydrocodone in rat sera fed 6-O-BocGlu(OtBu)-hydrocodone and 6-O-BocLys(NHBoc)hydrocodone was observed (FIG. 16). The AUC's for both amino acid/hydrocodone conjugates are 75% of hydrocodone's AUC.

The stability of the amino acid/narcotic conjugates can be increased by tethering it to a larger peptide via the nitrogen on the amino acid residue. This will also extend the absorption of the orally administered drug. For instance, the dipeptides added to hydrocodone include GluGlu, LeuGlu, AlaPro, GluPro and GluLeu.

Example 10

Preparation of Ala-Pro-Hydrocodone

| Reagents | MW | Weight | mmoles | Molar Equivalents |
|---|---|---|---|---|
| Pro-Hydrocodone | 468 | 0.25 g | 0.53 | 1.0 |
| Boc-Ala-OSu | 286 | 0.33 g | 1.2 | 2.26 |
| NMM | 101 | 0.50 ml | 5.38 | 10.2 |
| DMF | — | 10 ml | — | — |

Ala-Pro-Hydrocodone

To a solution of Pro-Hydrocodone in DMF was added NMM followed by Boc-Ala-OSu. The solution was stirred at ambient temperatures for 18hours. Solvent was removed. Crude material was purified using preparative HPLC. (Phenomenex Luna C18, 30×250 mm, 5 μM, 100 Å; Gradient: 100 water/0 0.1% TFA-MeCN→0/100; 30 ml/min.). Solid was collected as a slightly yellow powder (0.307 g, 85% yield): $^1$H NMR (DMSO-$d_6$) δ 1.16 (d, 3H), 1.35 (s, 9H), 1.51 (m, 2H), 1.86-2.10 (m, 6H), 2.50 (m, 1H), 2.54 (m, 1H), 2.69 (m, 1H), 2.88 (s, 3H), 3.02 (dd, 1H), 3.26 (d, 1H), 3.55 (m, 1H), 3.67 (m, 1H), 3.72 (s, 3H), 3.80 (s, 1H), 4.25 (m, 1H), 4.43 (d, 1H), 5.01 (s, 1H), 5.59 (d, 1H), 6.75 (d, 1H), 6.88 (d, 1H), 6.99 (t, 1H), 9.91 (br s, 1H).

To the Boc-Ala-Pro-Hydrocodone (0.100 g) was added 10 mil of 4N HCl in dioxane. The resulting mixture was stirred at ambient temperatures for 18 hours. Solvent was removed and final product dried under vacuum. Solid was collected as a slightly yellow solid (0.56 g, 71% yield): $^1$H NMR (DMSO-$d_6$) δ 1.38 (s, 3H), 1.48 (t, 1H), 1.80-2.29 (m, 8H), 2.65 (m, 1H), 2.80 (s, 3H), 2.96 (m, 3H), 3.23 (m, 2H), 3.76 (s, 3H), 3.92 (s,1H), 4.22 (s, 1H), 4.53 (s, 1H), 5.00 (s, 1H), 5.84 (d, 1H), 6.77 (d, 1H), 6.86 (d, 1H), 8.25 (br s, 3H).

Example 11

Preparation of Gly-Gly-Gly-Gly-Leu-Hydrocodone (SEQ ID NO: 1)

| Reagents | MW | Weight | mmoles | Molar Equivalents |
|---|---|---|---|---|
| Gly-Gly-Leu-Hydrocodone | 599 | 0.580 g | 0.970 | 1.0 |
| Boc-Gly-Gly-OSu | 329 | 0.638 g | 1.94 | 2.0 |
| NMM | 101 | 1.06 ml | 9.70 | 10 |
| DMF | — | 20 ml | — | — |

Gly-Gly-Gly-Gly-Leu-Hydrocodone (SEQ ID NO: 1)

To a solution of Gly-Gly-Leu-Hydrocodone in DMF was added NMM followed by Boc-Gly-Gly-OSu. The solution was stirred at ambient temperatures for 18 hours. Solvent was removed. Crude material was purified using preparative HPLC (Phenomenex Luna C18, 30×250 mm, 5 μM, 100 Å; Gradient: 85 water/15 0.1% TFA-MeCN→50/50; 30 ml/min.). Solid was collected as a slightly yellow powder (0.304 g, 37% yield).

To the Boc-Gly-Gly-Gly-Gly-Leu-Hydrocodone (SEQ ID NO: 1) (0.304 g) was added 25 ml of 4N HCl in dioxane. The resulting mixture was stirred at ambient temperatures for 18 hours. Solvent was removed and final product dried under vacuum. Solid was collected as a slightly yellow solid (0.247 g, 97% yield): $^1$H NMR (DMSO-$d_6$) δ 0.87 (m, 6H), 1.23 (s, 1H), 1.51-1.86 (m, 4H), 2.18 (m, 1H), 2.71 (m, 2H), 2.77 (s, 3H), 2.96 (m, 2H), 3.17 (m, 2H), 3.61 (s, 3H), 3.81-3.84 (m, 10H), 4.22 (m, 1H), 4.36 (m, 1H), 5.09 (m, 1H), 5.59 (d, 1H), 6.74 (dd, 2H), 8.16 (br s, 4H), 8.38 (br s, 1H), 8.74 (br s, 1H), 11.42 (br s, 1H).

Example 2

Preparation of Gly-Gly-Leu-Hydrocodone

| Reagents | MW | Weight | mmoles | Molar Equivalents |
|---|---|---|---|---|
| Leu-Hydrocodone | 484 | 2.21 g | 4.56 | 1.0 |
| Boc-Gly-Gly-OSu | 329 | 3.00 g | 9.12 | 2.0 |
| NMM | 101 | 5.0 ml | 45.6 | 10 |
| DMF | — | 100 ml | — | — |

Gly-Gly-Leu-Hydrocodone

To a solution of Leu-Hydrocodone in DMF was added NMM followed by Boc-Gly-Gly-OSu. The solution was stirred at ambient temperatures for 18 hours. Solvent was removed. Crude material was purified using preparative HPLC. (Phenomenex Luna C18, 30×250mm, 5 μM, 100 Å; Gradient: 90 water/10 0.1% TFA-MeCN→0/100; 30 ml/min.). Solid was collected as a slightly yellow powder (2.08 g, 73% yield): $^1$H NMR (DMSO-d6) δ 0.88 (dd, 6H), 1.38 (s, 9H), 1.53-1.72 (m, 5H), 1.89 (d, 1H), 2.15 (m, 1H), 2.67 (m, 2H), 2.94 (s, 3H), 3.05 (m, 2H), 3.25 (m, 2H), 3.56 (d, 3H), 3.76 (s, 6H), 3.98 (s, 1H), 4.35 (q, 1H), 5.04 (s, 1H), 5.59 (d, 1H), 6.77 (d, 1H), 6.85 (d, 1H), 7.04 (t, 1H), 8.01 (t, 1H), 8.30 (d, 1H), 9.99 (br s, 1H).

To the Boc-Gly-Gly-Leu-Hydrocodone (2.08 g) was added 50 ml of 4N HCl in dioxane. The resulting mixture was stirred at ambient temperatures for 18 hours. Solvent was removed and final product dried under vacuum. Solid was collected as a slightly yellow solid (1.72 g, 86% yield): $^1$H NMR (DMSO-d6) δ 0.89 (dd, 6H), 1.50-1.87 (m, 5H), 2.26 (m, 2H), 2.66 (m, 2H), 2.82-2.97 (m, 5H), 3.21 (m, 2H), 3.60 (m, 4H), 3.88 (m, 5H), 4.37 (m, 1H), 5.04 (s, 1H), 5.60 (s, 1H), 6.79 (d, 2H), 8.07 (br s, 3H), 8.54 (br s, 1H), 8.66 (br s, 1H), 11.29 (br s, 1H).

Example 13

Preparation of Leu-Hydrocodone

| Reagents | MW | Weight | mmoles | Molar Equivalents |
|---|---|---|---|---|
| 1. Hydrocodone | 299 | 1.00 g | 3.34 | 1.0 |
| 1. LiN(TMS)$_2$ in THF | 1 M | 10.5 ml | 10.5 | 3.15 |
| 1. THF | — | 25 ml | — | — |
| 2. Boc-Leu-OSu | 328 | 3.28 g | 10.0 | 3.0 |

Leu-Hydrocodone

To a solution of hydrocodone in THF was added LiN(TMS)$_2$ in THF via syringe. The solution was stirred at ambient temperatures for 5 minutes then Boc-Leu-OSu was added. The resulting reaction mixture was stirred at ambient temperatures for 18 hours. Reaction was neutralized to pH 7 with 6M HCl. Solvent was removed. Crude material was taken up in $CHCl_3$ (100 ml), washed with sat. $NaHCO_3$ (3×100 ml), dried over $MgSO_4$, filtered, and solvent removed. Solid was collected as a yellow powder (1.98 g, 95% yield): $^1$H NMR (DMSO-d6) δ 0.86 (dd, 6H), 1.31 (s, 9H), 1.46 (s, 2H), 1.55 (m, 2H), 1.69 (m, 1H), 1.87 (dt, 1H), 2.07 (dt, 2H), 2.29 (s, 3H), 2.43 (m, 2H), 2.93 (d, 1H), 3.11 (s, 1H), 3.72 (s, 3H), 3.88 (dt, 1H), 4.03 (dt, 1H), 4.87 (s, 1H), 5.51 (d, 1H), 6.65 (d, 1H), 6.73 (d, 1H), 6.90 (s, 1H).

To the Boc-Leu-Hydrocodone was added 25 ml of 4N HCl in dioxane. The resulting mixture was stirred at ambient temperatures for 18 hours. Solvent was removed and final product dried under vacuum. Solid was collected as a slightly yellow solid (1.96 g, 97% yield): 1H NMR (DMSO-d6) δ 0.94 (d, 6H), 1.52 (m, 1H), 1.75-1.90 (m, 4H), 2.22 (dt, 1H), 2.34 (dt, 1H), 2.64 (q, 1H), 2.75 (s, 3H), 2.95-3.23 (m, 4H), 3.74 (s, 3H), 3.91 (d, 1H), 4.07 (s, 1H), 5.10 (s, 1H), 5.72 (d, 1H), 6.76 (d, 1H), 6.86 (d, 1H), 8.73 br s, 3H).

Example 14

Analgesia of GlyGlyGlu-HC and ProProLeu-HC vs. HC Subcutaneously Injected

Peptide-narcotic conjugates GlyGlyGlu-HC and ProProLeu-HC and an equivalent amount of HC contained in the conjugates were subcutaneously administered separately to male Sprague-Dawley rats (~250 g). The level of analgesia was scored by the PLL (paw lick latency) method using the hot plate nociceptive model as described (Tomkins, D. M., et al. J Pharmacol Experimental Therapeutics, 1997, 280:1374-1382). Table 10 shows the latency response of GlyGlyGlu-HC vs. HC. Basal PLL times of untreated rats were subtracted from the conjugate and hydrocodone PLLs. At thirty minutes analgesia of GlyGlyGlu-HC. was 54% and at 45 minutes was 8%, when PPLs above basal level were compared to HC. indicating that analgesia was significantly inhibited by the attached tripeptide. The latency response of ProProLeu-HC vs. HC is shown in FIG. 21 and Table 11. PLL times above 0 hour basal level of pretreated rats is was scored at 15, 30, 45, and 60 minutes. At the thirty minute peak of analgesia ProProLeu-HC. was 9% of that for hydrocodone. The PPL latency score of ProProLeu-HC gradually rose over time, however, at 60 minutes was still only 43% of the hydrocodone. (note: a cutoff time of 45 seconds was used in the PLL scoring in order to minimaize any harm to the animals. Most of the hydrocodone treated animals reached the maximum 45 seconds at peak analgesia).

TABLE 10

Paw Lick Latency of GlyGlyGlu-HC vs. Hydrocodone

| | 30 minutes | | | 45 minutes | | |
|---|---|---|---|---|---|---|
| Sample | PLL | Delta | Percent | PLL | Delta | Percent |
| Control | 6.5 | 0 | NA | 6.8 | 0 | NA |
| HC | 40 | 34 | 100 | 26.7 | 19.9 | 100 |
| GGE-C | 24.5 | 18 | 54 | 8.4 | 1.6 | 8 |

TABLE 11

Paw Lick Latency of ProProLeu-HC vs. Hydrocodone

| Drug | Basal (0 h) | 15 min. | 30 min | 45 min. | 60 min. |
|---|---|---|---|---|---|
| Hydrocodone | 5.5 | 25.5 | 42.4 | 36.3 | 26.6 |
| PPL-HC | 6.0 | 10.3 | 9.4 | 13.7 | 15.1 |

TABLE 12

Paw Lick Latency of Peptide-HCs vs. Hydrocodone

| Drug | Basal (0 h) | 15 min. | 30 min | 60 |
|---|---|---|---|---|
| Hydrocodone | 5.6 | 31.9 | 24.5 | 15.1 |
| LLL-HC | 4.1 | 5.7 | 3.9 | 3.2 |
| PPI-HC | 4.1 | 4.9 | 5.2 | 5.6 |
| GGGGL-HC (SEQ ID NO: 1) | 7.5 | 6.8 | 5.6 | 3.6 |
| GGGGL-HC2X (SEQ ID NO: 1) | 2.2 | 3 | 5.6 | 5 |

The latency response of LeuLeuLeu-HC, ProProIle-HC, GlyGlyGlyGlyLeu-HC, (SEQ ID NO: 1) and GlyGlyGlyGlyLeu-HC (SEQ ID NO: 1) (2× the equivalent dose) is shown in Table 12 and FIG. 22. PLL times above 0 hour basal level of pretreated rats was scored at 15, 30, and 60 minutes. At the thirty minute peak of analgesia hydrocodone was the only test group that showed any response. The PPL latency scores of the peptide conjugates did not rise above the basal response, including the GlyGlyGlyGly-HC treated group that received twice the hydrocodone control dose.

Example 15

Active Agent List

The active agent that is attached to the carrier peptide can have one or more of different functional groups. The functional groups include an amine, carboxylic acid, alcohol, ketone, amido (or its chemical equivalent),thiol or sulfate. Examples of these active agents, their functional groups and site of attachment to the carrier peptide is provided in the section below. One skilled in the art would recognize the techniques necessary to covalently attach a peptide to the active agents as described through the application.

Acetaminophen with Codeine

Acetaminophen is a known pharmaceutical agent that is used in the treatment of minor aches and pains. Its chemical name is N-acetyl-p-aminophenol. It is often used in combination with codeine, whose chemical name is 7,8-didehydro-4,5-α-epoxy-3-methoxy-17-methylmephominan-6α-ol. Both are commercially available and readily manufactured using published synthetic schemes by those of ordinary skill in the art.

In the present invention, both acetaminophen and codeine are covalently attached to the peptide via their hydroxyl groups.

Codeine

Codeine is a known pharmaceutical agent that is used in the treatment of pain. The composition of the invention comprises codeine covalently attached to a peptide.

In the present invention, codeine is covalently attached to the peptide via the hydroxyl group.

Dihydrocodeine

Dihydrocodeine is a known pharmaceutical agent that is used in the treatment of pain. The composition of the invention comprises dihydrocodeine covalently attached to a peptide.

In the present invention, dihydrocodeine is covalently attached to the peptide via the hydroxyl group.

Codeine and Guaifenesin

Codeine and guaifenesin is a known pharmaceutical agent that is used in the treatment of coughs. The composition of the invention comprises codeine and guaifenesin covalently attached to a peptide via the hydroxyls of either active agent.

Codeine and Promethazine

Codeine and promethazine are known pharmaceutical agents used in the treatment of coughs. The composition of the invention comprises codeine and promethazine covalently attached to a peptide via functional groups specified in the active agent's respective catagory.

Codeine, Guaifenesin and Pseudoephidrine

Codeine, guaifenesin and pseudoephidrine are used in the treatment of coughs and colds. The composition of the invention comprises codeine, guaifenesin and pseudoephidrine covalently attached to a peptide peptide via functional groups specified in the active agent's respective catagory.

Codeine, Phenylephrine and Promethazine

Codeine, phenylephrine and promethazine is a known pharmaceutical agent that is used in the treatment of coughs and colds. The composition of the invention comprises codeine, phenylephrine and promethazine covalently attached to a peptide via functional groups specified in the active agent's respective catagory.

Fentanyl

Fentanyl is a known pharmaceutical agent that is used in the treatment of pain. It is both commercially available and readily manufactured using published synthetic schemes by those of ordinary skill in the art. Its structure is:

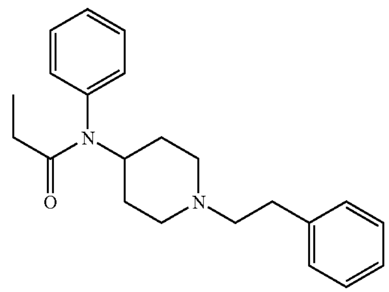

In the present invention, the fentanyl or modified fentanyl is covalently attached to the peptide via a linker. This linker may be a small molecule containing 2-6 carbons and one or more functional groups (such as amines, amides, alcohols, or acids) or may be made up of a short chain of either amino acids or carbohydrates.

Acetaminophen and Hydrocodone

Acetaminophen and hydrocodone is a known pharmaceutical agent that is used in the treatment of pain. The chemical name of acetaminophen is N-acetyl-p-aminophenol. The composition of the invention comprises acetaminophen and hydrocodone covalently attached to a peptide.

Chlorpheniramine and Hydrocodone

Chlorpheniramine and hydrocodone is a known pharmaceutical agent that is used in the treatment of pain. The composition of the invention comprises chlorpheniramine and hydrocodone covalently attached to a peptide.

Guaifenesin and Hydrocodone

Guaifenesin and hydrocodone is a known pharmaceutical agent that is used in the treatment of coughs. The composition of the invention comprises guaifenesin and hydrocodone covalently attached to a peptide using functional groups specifally described in the active agents respective category.

Himatropine and Hydrocodone

Himatropine and hydrocodone is a known pharmaceutical agent that is used in the treatment of pain. The composition of the invention comprises himatropine and hydrocodone covalently attached to a peptide using functional groups specifally described in the active agents respective category.

Hydrocodone and Phenylpropanolamine

Hydrocodone and phenylpropanolamine are used in the treatment of coughs and colds. The composition of the invention comprises hydrocodone and phenylpropanolamine covalently attached to a peptide.

In the present invention, hydrocodone and phenylpropanolamine is covalently attached to the peptide via one of the hydroxyl groups. Alternatively, phenylpropanolamine can be covalently attached to the peptide via the amino group.

Ibuprofen and Hydrocodone

Ibuprofen and hydrocodone are used in the treatment of pain. The structure of ibuprofen is:

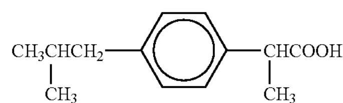

The composition of the invention comprises ibuprofen and hydrocodone covalently attached to a peptide using functional groups specifically described in the active agents respective category.

Hydrocodone

Hydrocodone is a known pharmaceutical agent that is used in the treatment of pain. The composition of the invention comprises hydrocodone covalently attached to a peptide.

In the present invention, hydrocodone is covalently attached to the peptide via a ketone group and a linker. This linker may be a small linear or cyclic molecule containing 2-6 atoms with one or more heteroatoms and one or more functional groups (such as amines, amides, alcohols or acids). For example, glucose would be suitable as a linker. Alternatively, hydrocodone may be attached directly through an enolate.

Hydromorphone

Hydromorphone is a known pharmaceutical agent that is used in the treatment of cough and pain. Its structure is:

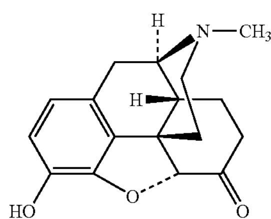

The composition of the invention comprises hydromorphone covalently attached to a peptide.

In the present invention, hydromorphone is covalently attached to the peptide via the hydroxyl group.

Morphine

Morphine is a known pharmaceutical agent that is used in the treatment of pain. Its structure is:

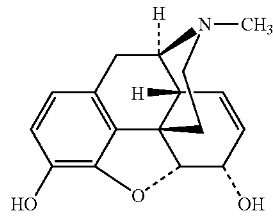

The composition of the invention comprises morphine covalently attached to a peptide.

In the present invention, morphine is covalently attached to the peptide via any of the hydroxyl groups.

Diacetylmorphine

Diacetylmorphine is a known pharmaceutical agent that is used in the treatment of pain. The composition of the invention comprises diacetylmorphine covalently attached to a peptide.

In the present invention, diacetylmorphine or modified diacetylmorphine is covalently attached to the peptide via a linker. This linker may be a small molecule containing 2-6 carbons and one or more functional groups (such as amines, amides, alcohols, or acids) or may be made up of a short chain of either amino acids or carbohydrates.

Dihydromorphine

Dihydromorphine is a known pharmaceutical agent that is used in the treatment of pain. The composition of the invention comprises dihydromorphine covalently attached to a peptide.

In the present invention, dihydromorphine is covalently attached to the peptide via the hydroxyl group.

Ethylmorphine

Ethylmorphine is a known pharmaceutical agent that is used in the treatment of pain. The composition of the invention comprises ethylmorphine covalently attached to a peptide.

In the present invention, ethylmorphine is covalently attached to the peptide via the hydroxyl group.

Oxycodone and Acetaminophen

Oxycodone and acetaminophen are used together in the treatment of pain.

The composition of the invention comprises oxycodone and acetaminophen covalently attached to a peptide.

Oxycodone

Oxycodone is a known pharmaceutical agent that is used in the treatment of pain. The structure of oxycodone is:

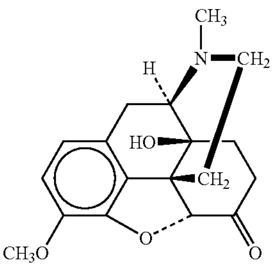

The composition of the invention comprises oxycodone covalently attached to a peptide.

In the present invention, oxycodone is covalently attached to the peptide via a ketone group and a linker. This linker may be a small linear or cyclic molecule containing 2-6 atoms with one or more heteroatoms and one or more functional groups (such as amines, amides, alcohols or acids). For example, glucose would be suitable as a linker. Alternatively, oxycodone may be attached directly through an enolate.

Propoxyphene

Propoxyphene is a known pharmaceutical agent that is used in the treatment of pain. It is a mild narcotic analgesic. It is both commercially available and readily manufactured using published synthetic schemes by those of ordinary skill in the art. The structure of propoxyphene is

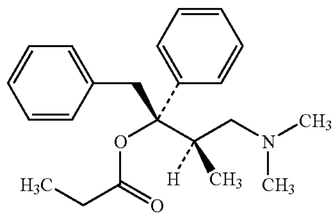

The composition of the invention comprises propoxyphene covalently attached to a peptide. In the present invention, propoxyphene or modified propoxyphene is covalently attached to the peptide via a linker. This linker may be a small molecule containing 2-6 carbons and one or more functional groups (such as amines, amides, alcohols, or acids) or may be made up of a short chain of either amino acids or carbohydrates.

Dextroamphetamine

Dextroamphetamine is a known pharmaceutical agent that is used in the treatment of narcolepsy and attention deficit hyperactivity disorder. It is both commercially available and readily manufactured using published synthetic schemes by those of ordinary skill in the art. Its structure is:

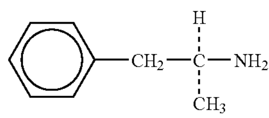

In the present invention, dextroamphetamine is covalently attached to the peptide via the amino group.

D-Methylphenidate

D-methylphenidate is a known pharmaceutical agent that is used in the treatment of attention deficit disorder. Its chemical name is (αR,2R)-α-phenyl-2-piperidineacetic acid methyl ester. Its structure is:

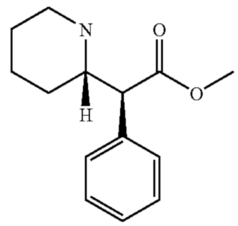

D-methylphenidate is the subject of U.S. Pat. No. 2,507,631 (1950) and WO 99/16439 (1999), based on U.S. application Number 937684 (1997), each of which is herein incorporated by reference, which describes how to make that drug.

In the present invention, D-methylphenidate is covalently attached to the peptide via the amino group.

Methylphenidate

Methylphenidate is a known pharmaceutical agent that is used in the treatment of attention deficit disorder. Its structure is:

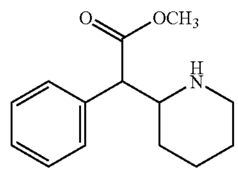

The composition of the invention comprises methylphenidate covalently attached to a peptide.

In the present invention, methylphenidate is covalently attached to the peptide via the amino group.

What is claimed is:

1. A pharmaceutical composition comprising: codeine; and a carrier covalently bound to the codeine in a manner that renders the codeine pharmacologically inactive or provides reduced pharmacological activity compared to codeine alone when administered parenterally, but provides pharmacologically effective amounts of codeine when administered orally; wherein the carrier is a peptide selected from the group consisting of Gly-Gly-Leu, Gly-Gly-Glu, Gly-Gly-Ile, Gly-Gly-Phe, Gly-Leu-Ile, Gly-Phe-Ile, Gly-Leu-Leu, Gly-Phe-Leu, Leu-Pro-Glu, Leu-Pro-Leu, Leu-Pro-Phe, Pro-Pro-Glu, Pro-Pro-Leu, Pro-Pro-Ile, Pro-Pro-Phe, Glu-Glu-Glu, Leu-Leu-Glu, Leu-Leu-Leu, $Gly_4$-Leu (SEQ ID NO: 1), $Glu_5$ (SEQ ID NO: 2), $Gly_4$-Ile (SEQ ID NO: 3), $Gly_4$-Phe (SEQ ID NO: 5), $Glu_2$-$Gly_2$ (SEQ ID NO: 6), $Glu_2$-$Gly_2$-Leu (SEQ ID NO: 8), or Glu2-Gly2-Ile (SEQ ID NO: 9); wherein the hydroxyl group of codeine is bound to the C-terminus of the carrier.

2. The composition of claim 1, wherein said composition is in tablet, a capsule, an oral suspension or an oral solution.

* * * * *